(12) United States Patent
Singh et al.

(10) Patent No.: US 11,181,454 B2
(45) Date of Patent: Nov. 23, 2021

(54) PHYSICAL AND CHEMICAL CHARACTERIZATION OF AEROSOLS WITH PHOTONIC WAVEGUIDES

(71) Applicant: Massachusetts Institute of Technology, Cambridge, MA (US)

(72) Inventors: Robin Singh, Cambridge, MA (US); Anuradha M. Agarwal, Weston, MA (US); Danhao Ma, Cambridge, MA (US); Peter X. Su, Somerville, MA (US); Brian W. Anthony, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 255 days.

(21) Appl. No.: 16/258,295

(22) Filed: Jan. 25, 2019

(65) Prior Publication Data
US 2019/0234850 A1    Aug. 1, 2019

Related U.S. Application Data

(60) Provisional application No. 62/622,470, filed on Jan. 26, 2018.

(51) Int. Cl.
*G01N 15/02* (2006.01)
*G01N 21/552* (2014.01)
(Continued)

(52) U.S. Cl.
CPC ......... *G01N 15/0205* (2013.01); *G01N 15/06* (2013.01); *G01N 21/39* (2013.01);
(Continued)

(58) Field of Classification Search
CPC .... G01N 15/0205; G01N 15/06; G01N 21/39; G01N 21/45; G01N 21/552;
(Continued)

(56) References Cited

U.S. PATENT DOCUMENTS

| 5,663,790 A | 9/1997 | Ekstroem et al. |
| 6,661,938 B2 | 12/2003 | Lim et al. |

(Continued)

FOREIGN PATENT DOCUMENTS

| WO | 2015189230 A1 | 12/2015 |

OTHER PUBLICATIONS

Soysal et al., "Aerosol mass concentration measurements: Recent advancements of real-time nano/micro systems," Journal of Aerosol Science, vol. 114, pp. 42-54, Dec. 2017.

(Continued)

*Primary Examiner* — Georgia Y Epps
*Assistant Examiner* — Don J Williams
(74) *Attorney, Agent, or Firm* — Theresa A. Lober

(57) ABSTRACT

A photonic aerosol particle sensor includes a plurality of photonic waveguide resonators each having a photonic waveguide disposed along a separate waveguide resonator path and each photonic waveguide having a lateral waveguide width different than the waveguide width of other photonic waveguide resonators in the plurality. All waveguides in the plurality of photonic waveguide resonators have a common vertical thickness and are formed of a common photonic waveguide material. An optical input connection couples light into the waveguide resonators. A particle input conveys aerosol particles toward the waveguide resonators and an aerosol particle output conveys aerosol particles away from the waveguide resonators. At least one optical output connection is optically connected to accept light out of the plurality of photonic waveguide resonators to provide a signal indicative of at least one characteristic of the aerosol particles to be analyzed.

30 Claims, 32 Drawing Sheets

(51) Int. Cl.
G01N 33/543 (2006.01)
G01N 21/39 (2006.01)
G01N 15/06 (2006.01)
G01N 21/77 (2006.01)
G01N 21/45 (2006.01)
G02B 6/12 (2006.01)
G01N 15/00 (2006.01)
G02B 6/293 (2006.01)

(52) U.S. Cl.
CPC ........... G01N 21/45 (2013.01); G01N 21/552 (2013.01); G01N 21/7703 (2013.01); G01N 21/7746 (2013.01); G01N 33/543 (2013.01); G01N 33/54373 (2013.01); G02B 6/12004 (2013.01); G02B 6/12007 (2013.01); *G01N 2015/0046* (2013.01); *G01N 2015/03* (2013.01); *G01N 2015/0693* (2013.01); *G02B 6/2938* (2013.01); *G02B 6/29338* (2013.01)

(58) Field of Classification Search
CPC ........... G01N 21/7703; G01N 21/7746; G01N 33/543; G01N 33/54373; G01N 15/0046; G01N 2015/0693; G02B 6/2938; G02B 6/29338; G02B 6/12004; G02B 6/12007
See application file for complete search history.

(56) References Cited

U.S. PATENT DOCUMENTS

| | | | |
|---|---|---|---|
| 6,751,368 B2 | 6/2004 | Lim et al. | |
| 7,447,410 B2 | 11/2008 | Agarwal et al. | |
| 7,796,262 B1 | 9/2010 | Wang et al. | |
| 9,046,650 B2 | 6/2015 | Lin et al. | |
| 9,915,785 B2 | 3/2018 | Lin et al. | |
| 10,006,809 B2 | 6/2018 | Hu et al. | |
| 2005/0265658 A1 | 12/2005 | Fan et al. | |
| 2007/0025410 A1 | 2/2007 | Agarwal et al. | |
| 2007/0091974 A1 | 4/2007 | Hu et al. | |
| 2007/0104410 A1 | 5/2007 | Ahn et al. | |
| 2007/0110357 A1 | 5/2007 | Hu et al. | |
| 2010/0014094 A1* | 1/2010 | Cole | G01N 21/3504 356/480 |
| 2011/0149285 A1* | 6/2011 | Chen | G01N 21/7746 356/432 |
| 2012/0012739 A1 | 1/2012 | Koch et al. | |
| 2012/0182552 A1 | 7/2012 | Heidrich et al. | |
| 2013/0243383 A1 | 9/2013 | Agarwal et al. | |
| 2013/0316368 A1 | 11/2013 | Vivien et al. | |
| 2014/0264030 A1 | 9/2014 | Lin et al. | |
| 2016/0282265 A1 | 9/2016 | Su et al. | |
| 2017/0242194 A1 | 8/2017 | Lin et al. | |
| 2018/0024072 A1 | 1/2018 | Han et al. | |

OTHER PUBLICATIONS

Singh et al., "Chemical Characterization of Aerosol Particles Using On-chip Photonic Cavity Enhanced Spectroscopy," ACS Sens., vol. 4, No. 3, pp. 571-577, Feb. 2019.
Kang et al., "Ge photodetector monolithically integrated with amorphous Si waveguide on wafer-bonded Ge-on-insulator substrate," Optics Express, vol. 26, No. 23, Nov. 2018.
Han et al., "On-chip mid-infrared gas detection using chalcogenide glass waveguide," Applied Physics Letters, vol. 28, No. 141106, p. 141106, Apr. 1-3, 2016.
Hu et al., "Fabrication and testing of planar chalcogenide waveguide integrated microfluidic sensor," Optics Express, vol. 15, No. 5, pp. 2307-2314, Mar. 2007.
Hu et al., "Planar waveguide-coupled, high-index-contrast, high-Q resonators in chalcogenide glass for sensing," Optics Letters, vol. 33, No. 21, pp. 2500-2502, Nov. 2008.
Kita et al., "On-Chip Infrared Spectroscopic Sensing: Redefining the Benefits of Scaling," IEEE Journal of Selected Topics in Quantum Electronics, vol. 23, No. 2, p. 5900110 1-10, Mar./Apr. 2017.
Lin et al., "Demonstration of high-Q mid-infrared chalcogenide glass-on-silicon resonators," Optics Letters, vol. 38, No. 9, pp. 1470-1472, May 2013.
Zhu et al., "Single virus and nanoparticle size spectrometry by whispering-gallery-mode microcavities," Optics Express, vol. 19, No. 17, p. 16195-16206, Aug. 2011.
Hu et al., "Cavity-Enhanced IR Absorption in Planar Chalcogenide Glass Microdisk Resonators: Experiment and Analysis," Journal of Lightwave Technology, vol. 27, No. 23, pp. 5240-5245, Dec. 2009.
Hu et al., "Design guidelines for optical resonator biochemical sensors," J. Opt. Soc. Am., vol. 26, No. 5, pp. 1032-1041, May 2009.
Canciamilla et al., "Photo-induced trimming of coupled ring-resonator filters and delay lines in As2S3 chalcogenide glass," Optics Letters, vol. 36, No. 20, pp. 4002-4004, Oct. 2011.
Hu et al., "Demonstration of chalcogenide glass racetrack microresonators," Optics Letters, vol. 33, No. 8, pp. 761-763, Apr. 2008.
Morichetti et al., "Alpha Radiation Effects on Silicon Oxynitride Waveguides," ACS Photonics, vol. 3, No. 9, pp. 1569-1574, Aug. 2016.
Kita et al., "Suspended chalcogenide microcavities for ultra-sensitive chemical detection," 2016 IEEE Sensors, Orlando, Fl, pp. 1-3, Oct. 30, 2016-Nov. 3, 2016.
Özdemir et al., "Highly sensitive detection of nanoparticles with a self-referenced and self-heterodyned whispering-gallery Raman microlaser," PNAS, vol. 111, No. 37, pp. E 3836-3844, Sep. 2014.
"A basic guide to particle characterization," Malvern Panalytical Ltd., Whitepaper, pp. 1-24, 2015.
Zhu et al., "On-chip single nanoparticle detection and sizing by mode splitting in an ultrahigh-Q microresonator," Nature Photonics, vol. 4, pp. 1-23, Jan. 2010.
Tao et al., "Hybrid Photonic Cavity with Metal-Organic Framework Coatings for the Ultra-Sensitive Detection of Volatile Organic Compounds with High Immunity to Humidity," Scientific Reports, vol. 7, No. 41640, pp. 1-8, Jan. 2017.
Schweinsberg et al., "An environmental sensor based on an integrated optical whispering gallery mode disk resonator," Sensors and Actuators B, vol. 123, No. 2, pp. 727-732, May 2007.
Armani et al., "Ultra-high-Q toroid microcavity on a chip," Letters to Nature, vol. 42, pp. 925-928, Feb. 2003.
Passaro et al., "Photonic resonant microcavities for chemical and biochemical sensing," RSC Advances, vol. 3, pp. 25-44, Oct. 2012.
Zhang et al., "A Micro Aerosol Sensor for the Measurement of Airborne Ultrafine Particles," Sensors, vol. 16, No. 3, pp. 399, Mar. 1-9, 2016.
Ma et al., "SiC-on-insulator on-chip photonic sensor in a radiative environment," IEEE Sensors, pp. 1-3, Oct. 2016.
Szymanski et al., "A new method for the simultaneous measurement of aerosol particle size, complex refractive index and particle density," Measurement Science and Technology, vol. 13, pp. 303-307, Feb. 2002.
Singh et al., "Towards on-chip mid infrared photonic aerosol spectroscopy," Applied Physics Letters, vol. 113, No. 23, p. 231107, Dec. 1-4, 2018.
PCT/US2019/015276 International Search Report, Form PCT/ISA/210 First Sheet, Second Sheet pp. 1-2, and patent family annex, Apr. 2019.
PCT/US2019/015276, Written Opinion of the International Searching Authority, Cover Sheet, Form PCT/ISA/237 1-2, Separate sheet, Sheets 1-11, Jul. 2020.
Singh, "Whispering Photons: On-Chip Biophotonic Integrated Circuits for Point-of-Care Diagnostics," Thesis in Master of Science in Mechanical Engineering, Massachusetts Institute of Technology, Jun. 2019.

* cited by examiner

FIG. 9A

700 nm-wide ring resonator

| Number of Particles | 100 nm | 200 nm | 400 nm | 600 nm | 800 nm | 1000 nm |
|---|---|---|---|---|---|---|
| 6 | 0.1909 | 0.1643 | 0.1201 | 0.1617 | 0.1688 | 0.174 |
| 5 | 0.1916 | 0.1675 | 0.126 | 0.1656 | 0.1714 | 0.176 |
| 4 | 0.1766 | 0.1636 | 0.1266 | 0.1487 | 0.1662 | 0.1714 |
| 3 | 0.1701 | 0.1682 | 0.1266 | 0.1474 | 0.1565 | 0.161 |
| 2 | 0.1701 | 0.1669 | 0.1143 | 0.1351 | 0.1344 | 0.1422 |
| 1 | 0.1753 | 0.1727 | 0.126 | 0.1409 | 0.1383 | 0.1461 |

Particle radius

FIG. 9B

800 nm-wide ring resonator

| Number of Particles | | | | | | |
|---|---|---|---|---|---|---|
| 6 | 0.2537 | 0.2473 | 0.183 | 0.2245 | 0.2317 | 0.2369 |
| 5 | 0.2544 | 0.2499 | 0.1889 | 0.2284 | 0.2343 | 0.2388 |
| 4 | 0.2486 | 0.2398 | 0.1895 | 0.2116 | 0.2291 | 0.2343 |
| 3 | 0.2453 | 0.2427 | 0.1895 | 0.2103 | 0.2194 | 0.2239 |
| 2 | 0.2336 | 0.2317 | 0.1772 | 0.1979 | 0.1973 | 0.2051 |
| 1 | 0.2349 | 0.2343 | 0.1889 | 0.2038 | 0.2012 | 0.209 |
| | 100 nm | 200 nm | 400 nm | 600 nm | 800 nm | 1000 nm |

Particle radius

FIG. 9C

900 nm-wide ring resonator

| Number of Particles | 100 nm | 200 nm | 400 nm | 600 nm | 800 nm | 1000 nm |
|---|---|---|---|---|---|---|
| 6 | 0.3001 | 0.2969 | 0.2554 | 0.2593 | 0.2625 | 0.293 |
| 5 | 0.3008 | 0.2988 | 0.2586 | 0.2619 | 0.2638 | 0.2943 |
| 4 | 0.2982 | 0.2943 | 0.2567 | 0.2535 | 0.2547 | 0.2774 |
| 3 | 0.2949 | 0.2936 | 0.2418 | 0.2496 | 0.247 | 0.2794 |
| 2 | 0.2697 | 0.2859 | 0.2385 | 0.2366 | 0.2463 | 0.256 |
| 1 | 0.2904 | 0.2872 | 0.2418 | 0.2398 | 0.2522 | 0.258 |

Particle radius

FIG. 10

| | Particle Radius 100 nm | | | | | | Particle Radius 200 nm | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 0.1753 | 0.1701 | 0.1701 | 0.1766 | 0.1916 | 0.1909 | 0.1727 | 0.1669 | 0.1682 | 0.1636 | 0.1675 | 0.1643 |
| R2 | 0.2349 | 0.2336 | 0.2453 | 0.2486 | 0.2544 | 0.2537 | 0.2343 | 0.2317 | 0.2427 | 0.2398 | 0.2499 | 0.2473 |
| R3 | 0.2904 | 0.2697 | 0.2949 | 0.2982 | 0.3008 | 0.3001 | 0.2872 | 0.2859 | 0.2936 | 0.2943 | 0.2988 | 0.2969 |
| | Number of Particles | | | | | | Number of Particles | | | | | |

FIG. 15C

| Resonator | Parameter | Value |
| --- | --- | --- |
| R1 | Radius of ring | 50 μm |
| R1 | Width of ring ($w_1$) | 700 nm |
| R1 | Thickness of the ring and bus | 400 nm |
| R1 | Width of the bus waveguide | 700 nm |
| R1 | Gap between ring and bus (center to center) | 500 nm |
| R2 | Radius of ring | 50 μm |
| R2 | Width of ring ($w_2$) | 800 nm |
| R2 | Thickness of the ring and bus | 400 nm |
| R2 | Width of the bus waveguide | 700 nm |
| R2 | Gap between ring and bus (center to center) | 500 nm |
| R3 | Radius of ring | 50 μm |
| R3 | Width of ring ($w_3$) | 900 nm |
| R3 | Thickness of the ring and bus | 400 nm |
| R3 | Width of the bus waveguide | 700 nm |
| R3 | Gap between ring and bus (center to center) | 500 nm |

FIG. 15D

| Resonator | Parameter | Value |
|---|---|---|
| R1 | Radius of ring | 30 μm |
| R1 | Width of ring ($w_1$) | 700 nm |
| R1 | Thickness of the ring and bus | 400 nm |
| R1 | Width of the bus waveguide | 700 nm |
| R1 | Gap between ring and bus (center to enter) | 500 nm |
| R2 | Radius of ring | 50 μm |
| R2 | Width of ring ($w_2$) | 800 nm |
| R2 | Thickness of the ring and bus | 400 nm |
| R2 | Width of the bus waveguide | 700 nm |
| R2 | Gap between ring and bus (center to center) | 500 nm |
| R3 | Radius of ring | 80 μm |
| R3 | Width of ring ($w_3$) | 900 nm |
| R3 | Thickness of the ring and bus | 400 nm |
| R3 | Width of the bus waveguide | 700 nm |
| R3 | Gap between ring and bus (center to center) | 500 nm |

FIG. 16C

| Resonator | Parameter | Value |
|---|---|---|
| R1 | Radius of ring | 200 μm |
| R1 | Width of ring ($w_1$) | 1.2 μm |
| R1 | Thickness of the ring and bus | 1.2 μm |
| R1 | Width of the bus waveguide | 1.5 μm |
| R1 | Gap between ring and bus (center to center) | 2.75 μm |
| R2 | Radius of ring | 200 μm |
| R2 | Width of ring ($w_2$) | 1.4 μm |
| R2 | Thickness of the ring and bus | 1.2 μm |
| R2 | Width of the bus waveguide | 1.5 μm |
| R2 | Gap between ring and bus (center to center) | 2.75 μm |
| R3 | Radius of ring | 200 μm |
| R3 | Width of ring ($w_3$) | 1.6 μm |
| R3 | Thickness of the ring and bus | 1.2 μm |
| R3 | Width of the bus waveguide | 1.5 μm |
| R3 | Gap between ring and bus (center to center) | 2.75 μm |

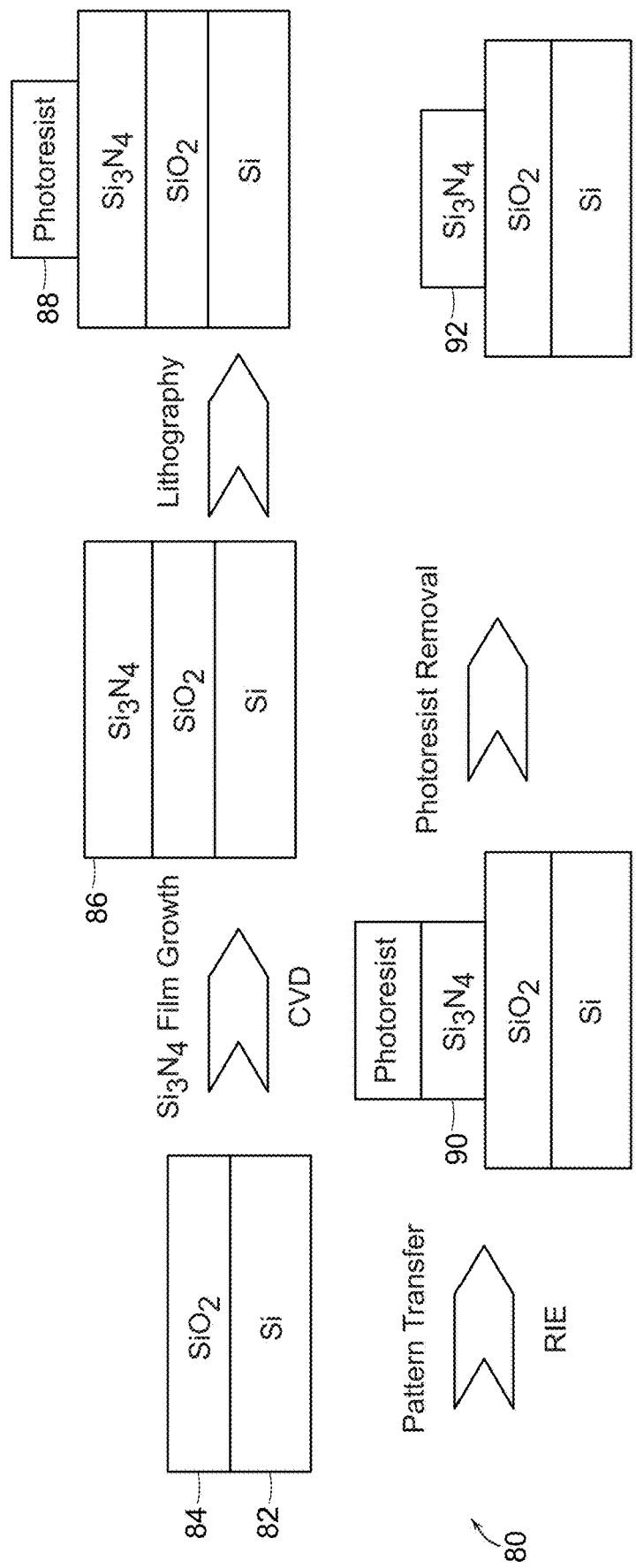

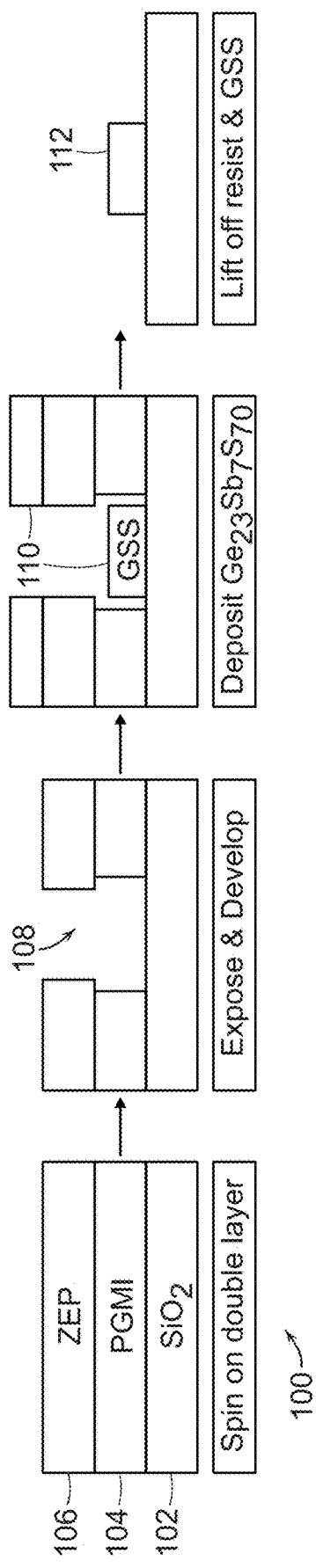

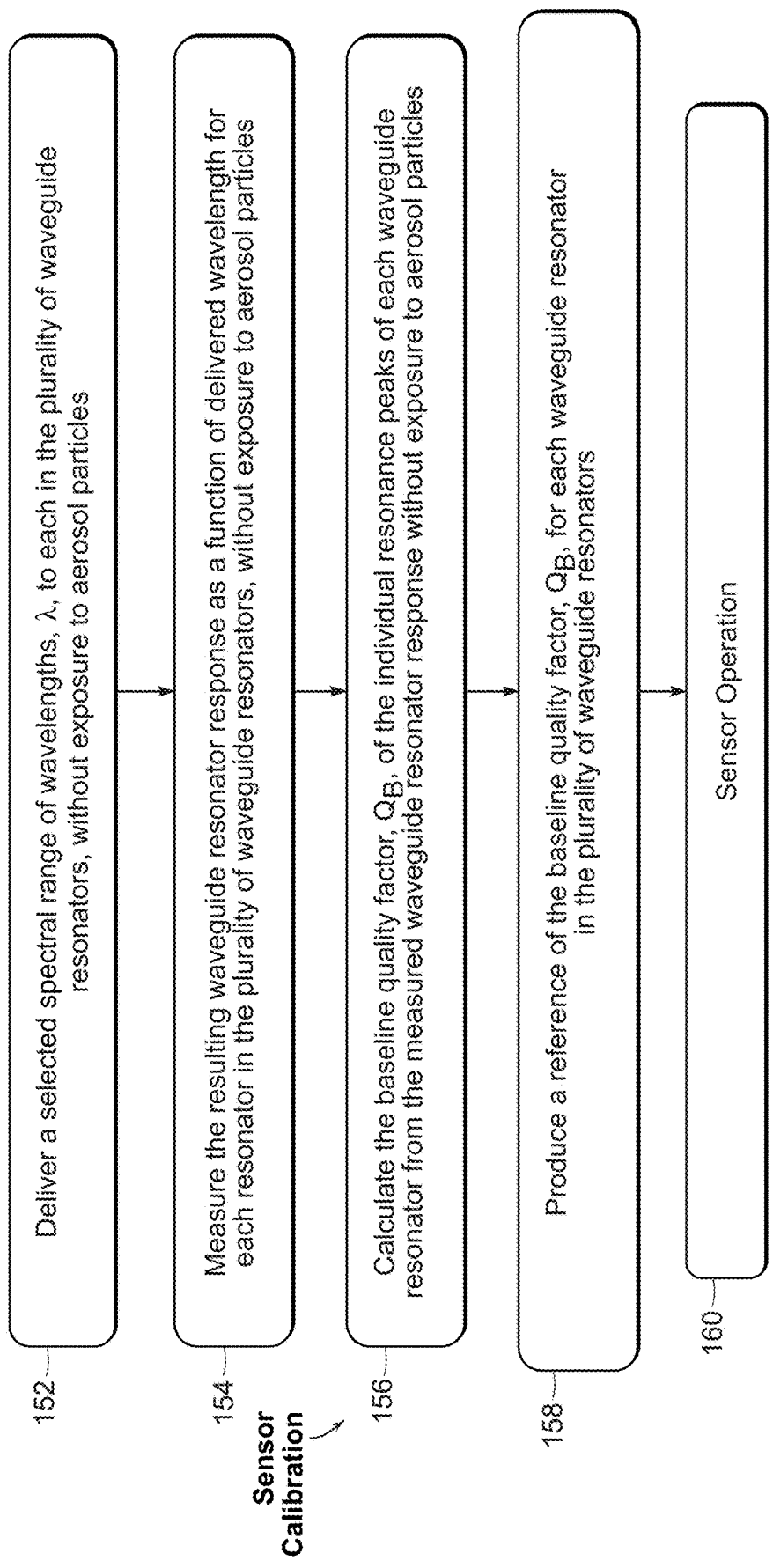

PHYSICAL AND CHEMICAL CHARACTERIZATION OF AEROSOLS WITH PHOTONIC WAVEGUIDES

CROSS-REFERENCE TO RELATED APPLICATION

This application claims the benefit of U.S. Provisional Patent Application No. 62/622,470, filed Jan. 26, 2018, the entirety of which is hereby incorporated by reference.

BACKGROUND

This invention relates generally to aerosol particle sensing, and more particularly relates to physical and chemical sensing of aerosol particles.

Aerosols consist of solid and/or liquid particles that are suspended in a gaseous medium. As such, aerosols can be formed naturally as well as artificially and controllably. Aerosol particles distributed in the atmosphere can have a significant role in the physio-chemistry of the natural environment, influencing air quality, climate, and transport of species, both intentionally and unintentionally, including the dispersal of industrial and pollutant species. The properties of aerosols are also important for scientific research, including nanotechnology research and pharmaceutical research, including, e.g., pulmonary and transdermal drug delivery and nano-scale microfluidic systems.

Aerosol particles distributed in the atmosphere can constitute a serious health threat depending on the aerosol particle chemistry, particle size, and particle count, or concentration. For example, depending on the particle size of a particular aerosol, the inhalation and deposition of the aerosol particles in a human lung airway can lead to dangerous respiratory complications; and aerosols that include particular functional groups can be especially dangerous. The comprehensive sensing and analysis of ambient aerosol particles are therefore becoming increasingly critical for addressing human health concerns, and particularly for addressing conditions in which it is important to monitor environmental pollution, industrial pollution or defense threats.

In scientific research and medical applications, the control of aerosol properties such as particle size and particle number count is critical for enabling controlled experimentation as well as for safe and effective medical therapies. For example, tight control of aerosol particle properties is important for enabling the precise pulmonary delivery of drug dosages within the respiratory tract. Similarly, transdermal drug delivery requires the use of highly-controlled nanoparticle-based aerosols for precise drug dosing. The analysis and control of microphysical and chemical properties of an aerosol are therefore becoming progressively more important as the requirements for aerosol particle drug delivery, nano-scale experimentation, and environmental monitoring increase and require higher precision.

Conventional aerosol particle sensors are generally based on optical or electrical sensing techniques in which aerosol particles are sensed by free-space methods of optical scattering and/or electrical mobility. For example, for determining physical aerosol characteristics, aerosol particles to be analyzed are typically disposed in an environment that enables the aerosol particles to interact with light waves; scattering of light that occurs due to such interaction is dependent on the aerosol particle size and aerosol particle number concentration. This conventional aerosol optical sensing technique has been shown for use as an optical aerosol particle counter, e.g., as a laser aerosol particle counter, for applications such as condensation particle counting. In general, while such optical-based aerosol sensing systems are functional, such optical-based aerosol sensing systems are often prohibitively expensive and/or are quite physically bulky, and for many applications, are limited by poor sensitivity.

Conventional chemical aerosol particle sensors generally employ a sensing method based on Fourier Transform Infrared (FTIR) spectroscopy, Raman spectroscopy, or fluorescent imaging. While these sensing techniques have had some success historically, these sensing techniques are increasingly unable to meet the needs of research and medicine, either because they require a physical sensing system that is too bulky for field testing, or because their sensitivity is inadequate when miniaturized to a hand-held form factor.

In an alternative paradigm, there has been shown the ability to detect and sense aerosol particles that are in the nanoscale regime using an optical whispering gallery mode resonator. A whispering gallery mode resonator exploits light that is disposed near to the surface of the resonator to sense species, such as a liquid analyte, that is in the vicinity of the resonator. Such a resonator has been widely used to sense liquid biological samples with very high sensitivity. But historically, in practice, resonator sensors have been limited in the particle size that can be sensed; only particles of no more than few nanometers, and well below about 200 nm in extent, can generally be sensed. Such resonator sensors are based on the sensing of splitting of optical modes, and as a result, require the use of optical resonators having a very high quality factor. In practice it is found that the fabrication of microresonators of such high quality factor is a challenging task, with poor repeatability, and therefore that such microresonator-based particle sensors cannot be reliably produced.

As a result, precise physio-chemical analysis of aerosol particles is yet to be provided in a system that can adequately address the needs of environmental field work, nano-scale research, medical and pharmaceutical science, and defense applications.

SUMMARY

There are provided herein aerosol particle sensors and methods for operating the aerosol particle sensors for aerosol analysis across a wide range of applications. A photonic aerosol particle sensor provided herein includes a plurality of photonic waveguide resonators. Each photonic waveguide resonator has a photonic waveguide that is disposed along a separate waveguide resonator path and each photonic waveguide has a lateral waveguide width that is different than the lateral waveguide width of other photonic waveguide resonators in the plurality of photonic waveguide resonators. All of the photonic waveguides in the plurality of photonic waveguide resonators have a common vertical thickness and are formed of a common photonic waveguide material. At least one optical input connection is provided for coupling light into each photonic waveguide in the plurality of photonic waveguide resonators. An aerosol particle input conveys aerosol particles to be analyzed toward the plurality of photonic waveguide resonators and an aerosol particle output conveys aerosol particles away from the plurality of photonic waveguide resonators. At least one optical output connection is optically connected to accept light out of the plurality of photonic waveguide resonators to provide a signal indicative of at least one characteristic of the aerosol particles to be analyzed.

With this aerosol particle sensor arrangement, there is provided a method for sensing aerosol particles. In the method, aerosol particles to be analyzed are conveyed toward a plurality of photonic waveguide resonators, each photonic waveguide resonator comprising a photonic waveguide disposed along a separate waveguide resonator path and having a lateral waveguide width that is different than the lateral waveguide width of other photonic waveguide resonators in the plurality of photonic waveguide resonators, all photonic waveguides in the plurality of photonic waveguide resonators having a common vertical thickness and formed of a common photonic waveguide material. Light is coupled into the plurality of photonic waveguide resonators while the aerosol particles are conveyed toward the plurality of photonic waveguide resonators, and light is coupled out of the plurality of photonic waveguide resonators while the aerosol particles are conveyed toward the plurality of photonic waveguide resonators. Light coupled out of the plurality of photonic waveguide resonators is detected and based on the detected light, there is determined a resonance peak wavelength of each photonic waveguide resonator in the plurality of photonic waveguide resonators in response to exposure to the aerosol particles.

The difference between a baseline resonance peak wavelength of each photonic waveguide resonator, characteristic of each photonic waveguide resonator absent exposure to the aerosol particles, and the determined resonance peak wavelength of each photonic waveguide resonator in response to exposure to the aerosol particles, is then calculated to specify a resonance peak wavelength shift value for each photonic waveguide resonator in response to exposure to the aerosol particles. The specified resonance peak wavelength shift values for the plurality of photonic waveguide resonators are then compared with calibration resonance peak wavelength shift values prespecified for the plurality of photonic waveguide resonators for at least one aerosol particle characteristic; and based on the comparison, at least one aerosol particle characteristic is determined.

The aerosol particle sensors and sensing methodology provided herein enables aerosol particle sensing across a wide range of aerosol particle sizes, particle number counts, and particle chemistry with a micro-scale sensing system. Other features and advantages of embodiments provided herein will be apparent from the following detailed description and accompanying figures, and from the claims.

BRIEF DESCRIPTION OF THE DRAWINGS

FIGS. 9A, 9B, and 9C are maps of the value of the shift in peak resonant wavelength for number of aerosol particles interacting with a waveguide ring resonator mapped to the radius of aerosol particles interacting with the waveguide ring resonator, for ring resonator waveguide widths of 700 nm, 800 nm, and 900 nm, respectively;

FIG. 10 is a map of the value of the shift in peak resonant wavelength for number of aerosol particles interacting with a waveguide ring resonator mapped to an aerosol particle radius of 100 nm and mapped to an aerosol particle radius of 200 nm, for ring resonators having waveguide widths of 700 nm, 800 nm, and 900 nm, here identified as R1, R2, and R3, respectively;

FIG. 15C is a table of a first example set of geometric values for waveguide ring resonator radius, resonator waveguide width, waveguide thickness, coupling bus waveguide width, and resonator-coupling bus gap, for a tandem set of n=3 ring resonators for the geometric values given in FIGS. 15A and 15B;

FIG. 15D is a table of a second example set of geometric values for waveguide ring resonator radius, resonator waveguide width, waveguide thickness, coupling bus waveguide width, and resonator-coupling bus gap, for a tandem set of n=3 ring resonators;

FIG. 16C is a table of example set of geometric values for waveguide ring resonator radius, resonator waveguide width, waveguide thickness, coupling bus waveguide width, and resonator-coupling bus gap, for a tandem set of n=3 ring resonators for the geometric values given in FIGS. 16A and 16B;

FIG. 5B illustrates a waveguide racetrack resonator 65 having a straight length extent, $L_c$, on each side of the resonator, between two curves 67 each having a curve radius, r. A waveguide bus 62 is disposed adjacent to and separated from the racetrack resonator to couple input light into the racetrack resonator in a coupling region 66. For some designs, a racetrack resonator can have a longer coupling region than a ring resonator, given the inclusion of a straight length of waveguide between the curved ends of the racetrack waveguide. For some applications, a racetrack waveguide resonator can therefore be preferred, but in general, either of a ring resonator and a racetrack resonator can be employed in embodiments provided herein.

In a resonant waveguide structure, as optical resonance is reached and maintained within the waveguide, the energy of the waveguide increases, and causes the electric field in the waveguide to be sensitive to any physical perturbation of the waveguide's evanescent electric field by the surrounding environment. This can be understood quantitatively by the following: the peak resonant wavelength corresponds to a dip in the transmission due to destructive interference of the transmitted light and waveguide resonator light coupling back to the coupling bus waveguide. With the input power given as $P_0$ and the starting resonance given as $Q_0$, the output power P and perturbed resonance Q are given as:

$$\begin{bmatrix} P \\ Q \end{bmatrix} = R \begin{bmatrix} P_0 \\ Q_0 \end{bmatrix} \quad (3)$$

$$R = \begin{pmatrix} t & jk \\ jk^* & t^* \end{pmatrix} \quad (4)$$

where, k and t are the mode coupling coefficient and transmission coefficient, respectively. For an absorption factor, a, and transmission factor, t, and with $\phi$ representing the phase of the light wave, the transmission coefficient, $T(\phi)$ is given by $$T(\phi) = \frac{a^2 + t^2 - 2at\cos\phi}{1 + a^2 t^2 - 2at\cos\phi}. \quad (5)$$

When represented in terms of the resonance ring circumference, L, and the refractive index of the optical mode supported in the waveguide, $n_{eff}$, $\phi$ can be represented as $$\frac{2\pi L n_{eff}}{\lambda}.$$

As explained above, when an aerosol particle in the vicinity of a resonator waveguide interacts with the evanescent electric field of the waveguide, the particle absorbs and scatters light waves associated with the evanescent electric field. Specifically, the resonance frequency and the quality factor of the resonator change as the interacting particle gets polarized in the electric field in which the particle at least partially overlaps. The polarizability of a physical particle is a strong function of the particle size. Thus, the resulting scattering and absorption losses in the electric field that is interior to the waveguide results in a change in the peak resonant frequency, i.e., a change in the peak resonant wavelength, of the waveguide resonator, as a function of the amount of physical particle matter in the vicinity of the waveguide.

Figure 4:
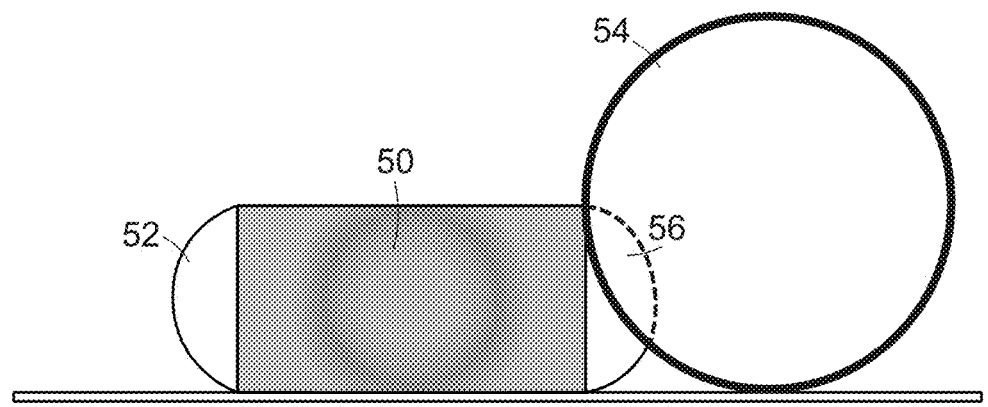
FIG. 4 is a schematic view of the cross section of an optical waveguide and the corresponding evanescent electric field of the waveguide when light propagates through the waveguide, with an aerosol particle partially interacting with the evanescent electric field of the waveguide.
Figure 5A:
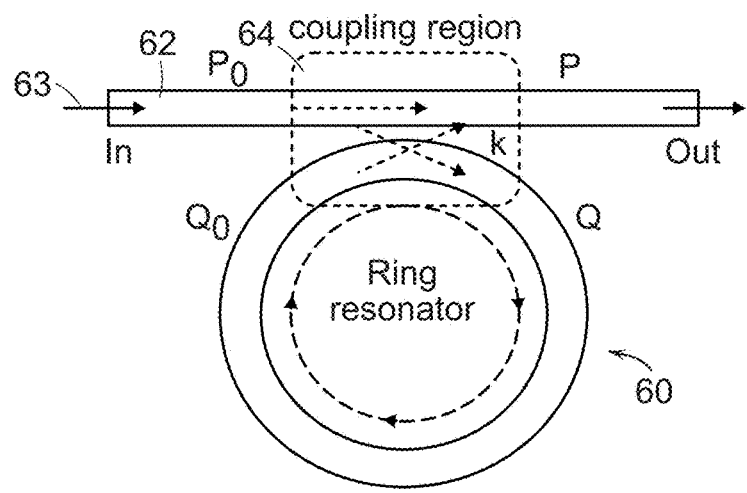
FIG. 5A is a schematic view of an optical waveguide ring resonator and associated optical bus.
Figure 5B:
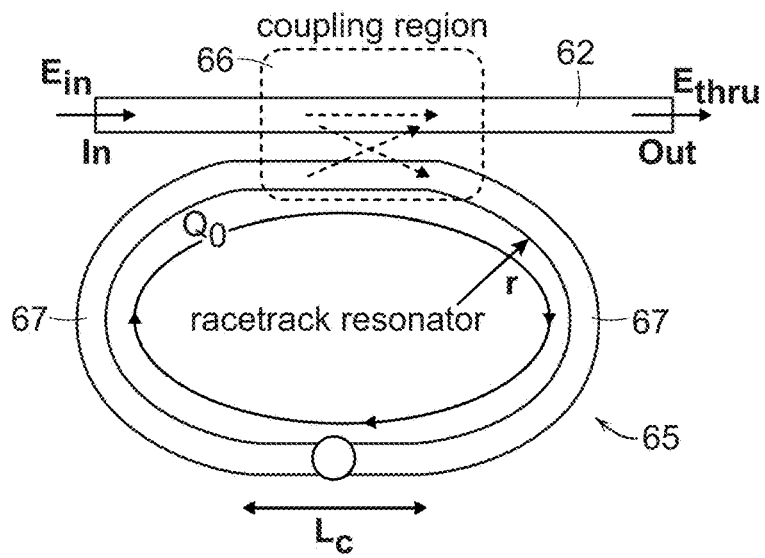
FIG. 5B is a schematic view of an optical waveguide racetrack resonator and associated optical bus.

Specifically, a particle in the vicinity of a ring waveguide changes the effective refractive index of the resonator waveguide, and it is this change in effective refractive index of the waveguide medium that causes a shift in the peak resonant wavelength of the resonant cavity formed by the resonator waveguide. The change in effective refractive index of the waveguide caused by a particle is dependent on the amount of particle matter that interacts with the tail of the evanescent electric field outside of the waveguide. As a result, particles of different sizes, presenting differing fractions of particle volume that are within the evanescent electric field of the waveguide, as shown in FIG. 4, interact with the evanescent electric field to differing extents and change the peak resonant wavelength of the resonator waveguide to a different extent.

The particles that are contained in aerosols of most interest for applications in environmental, medical, and pharmaceutical fields generally range size from about a few nanometers to tens of microns, i.e., a wide range of aerosols of interest include particles having an extent between about 2 nanometers and about 50 microns. But the evanescent electric field extent exterior to the surface of a waveguide resonator, i.e., the evanescent electric field penetration depth of a waveguide resonator, generally varies between a minimum distance of about 10 nanometers from the edge of a waveguide to a maximum distance of about 200 nanometers from the edge of the waveguide. As a result, aerosol particles having an extent greater than about 200 nanometers can only partially interact with the evanescent field in the vicinity of a waveguide resonator. This condition is shown in FIG. 4. The limited interaction of a portion of a particle and a waveguide resonator evanescent electric field is therefore not sufficient to characterize the particle based on the changes in waveguide resonator resonance wavelength and quality factor that are due only to a portion of the particle being within the evanescent electric field. As a result, the properties of particles that are larger than about 200 nanometers cannot be ascertained from a measurement of peak resonance shift of a single waveguide resonator.

Figure 6A:
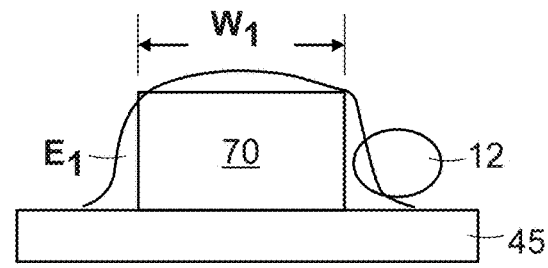
FIGS. 6A, 6B, and 6C are schematic cross-sectional views of three optical resonator waveguides and their corresponding evanescent electric fields interacting with an aerosol particle, for a first, largest waveguide width, a second, intermediate waveguide width, and a third, smallest waveguide width, respectively.
Figure 6B:
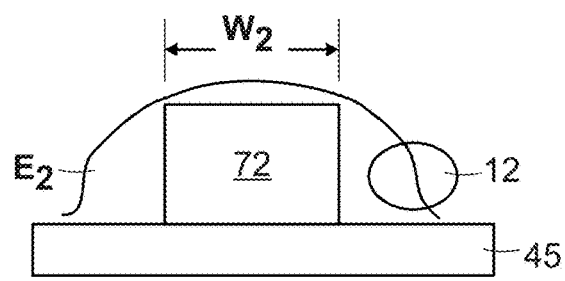
Figure 6C:
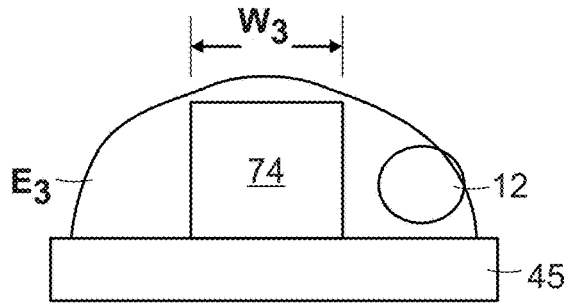

The inventors herein have discovered that this limitation in particle size sensing by a single waveguide resonator can be overcome by employing a plurality of at least two waveguide resonators that together operate as a set of tandem aerosol particle sensors, with each waveguide resonator in the plurality having a different wave guide width and correspondingly different evanescent electric field extent outside of the waveguide. Referring to FIGS. 6A-6C, in one example of such, there are employed three waveguide ring resonators in an aerosol sensor, with the three resonators including a resonant cavity waveguide 70, 72, 74, of a different waveguide width; the first waveguide 70 has a first width, $w_1$, and a first evanescent electric field $E_1$; the second waveguide 72 has a second width, $w_2$, and second evanescent electric field, $E_2$; and the third waveguide 74 has a third width, $w_3$, and a third evanescent electric field $E_3$. The first waveguide 70 has the largest waveguide width and thus the smallest evanescent electric field extent; the second waveguide 72 has a smaller waveguide width and a larger evanescent electric field extent; and the third waveguide 74 has the smallest width and thus the largest evanescent electric field extent.

Given aerosol particles 12, shown in FIGS. 6A-6C, all of the same size, that interact with the evanescent electric fields of the three different resonator waveguides 70, 72, and 74, a different shift in the peak resonance wavelength occurs for each of the three waveguides, because a different amount of evanescent electric field extent overlaps with particle matter volume. A unique set of three different peak resonant wavelength shifts therefore occurs for the aerosol particles 12 interacting with the three waveguide resonators.

Figure 7A:
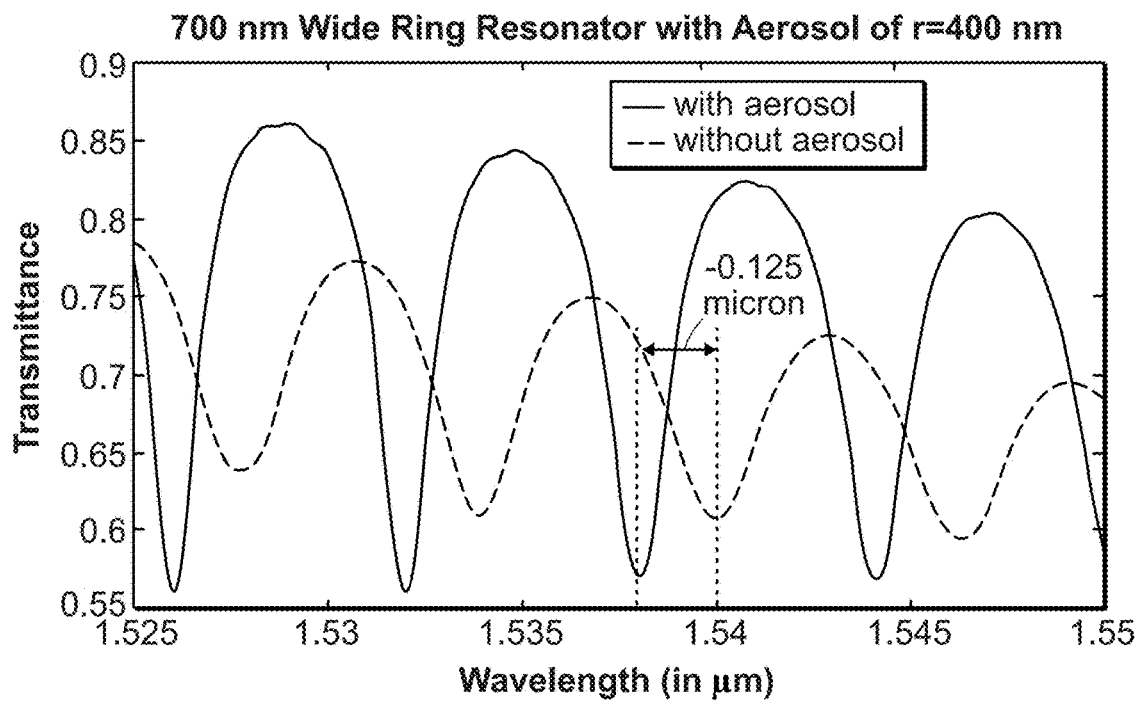
FIGS. 7A, 7B, and 7C are plots of simulated waveguide ring resonator transmittance as a function of wavelength when exposed to an aerosol of 400 nm-radius aerosol particles and without exposure to aerosol, for ring resonator waveguide widths of 700 nm, 800 nm, and 900 nm, respectively.
Figure 7B:
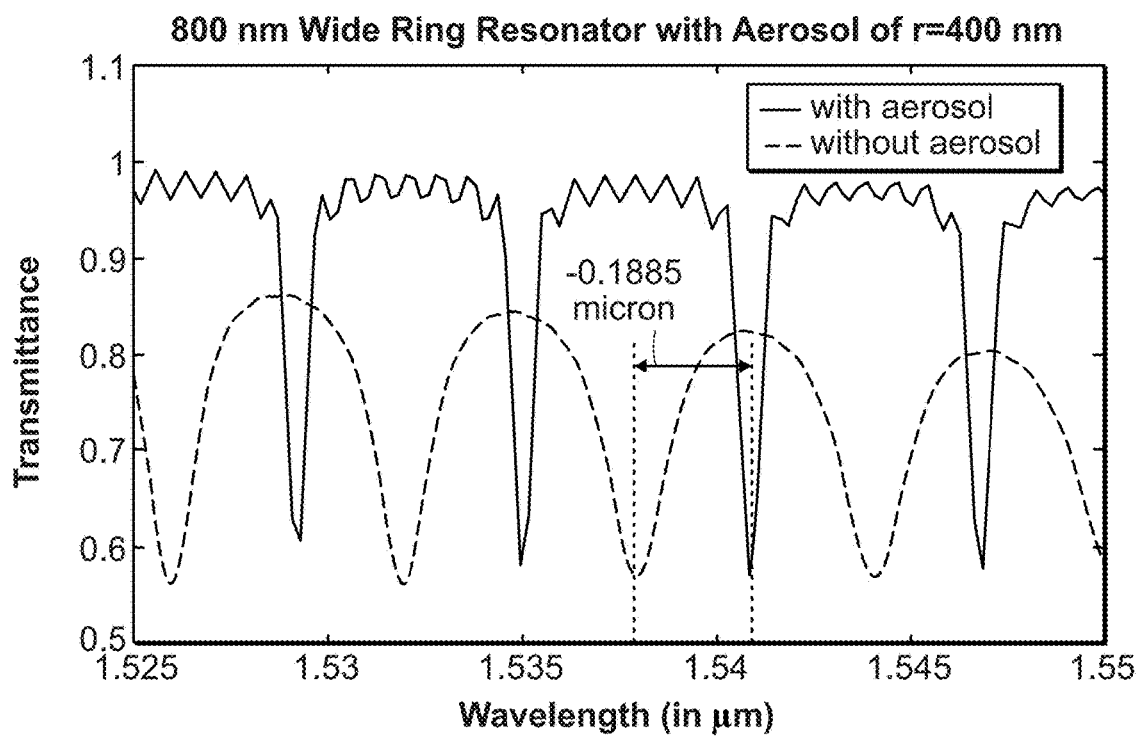
Figure 7C:
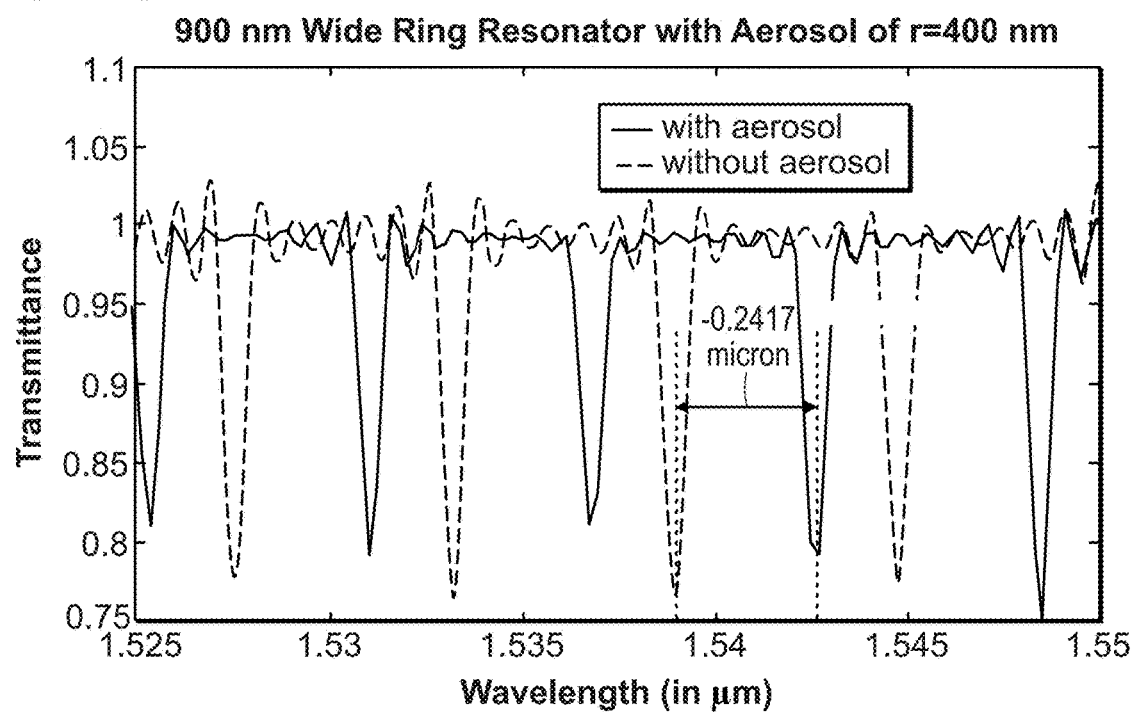

The plots of FIGS. 7A, 7B, and 7C demonstrate this quantitatively. Each of these FIGS. 7A-7C plots the optical transmittance of a ring waveguide resonator as a function of the wavelength of light propagating through the waveguide resonator, under conditions in which no particle is in the evanescent electric field of the resonator and in which the particle 12 (FIGS. 6A-6C) is in the evanescent electric field of the resonator, respectively, for three different waveguide resonator widths, namely, 700 nm-wide (7A), 800 nm-wide (7B), and 900 nm-wide (7C). This data is produced using a 2D finite difference time domain (FDTD) simulation, e.g., with a commercial simulation package such as FDTD Solutions, from Lumerical, Inc., Vancouver, BC, Canada. For the data shown here, a silicon nitride waveguide resonator on a silicon dioxide-coated substrate, operating in free space, is given a priori, e.g., with a coupling bus waveguide width of 800 nm, a resonator-coupling bus-gap of 500 nm, and an effective waveguide ring resonator radius of 30 microns.

With the data in the plots of FIGS. 7A, 7B, and 7C, the baseline peak resonant wavelength of each of the three waveguide resonators is identified, and the shift of that natural, baseline peak resonant wavelength to a shifted resonant wavelength caused by the presence of a particle is identified. The difference, in units of distance, between the natural and the shifted peak resonant wavelength is clear, and is different for each of the three waveguide resonators. As a result, the particle 12 (FIGS. 6A-6C) produces a unique peak resonant wavelength shift signature composed of the values of the shift in peak resonant wavelength for the three waveguide resonators. For this example, that signature can be given as: Shift 1: −0.125, Shift 2: −0.1885, Shift 3: −0.2417.

The peak resonant wavelength of a waveguide resonator is shifted not only by the size of a particle in the vicinity of a waveguide resonator, but also by number of particles within the evanescent electric field of the waveguide resonator. As the number of particles within the evanescent electric field of a waveguide resonator increases, the amount of particle matter volume interacting with the evanescent field correspondingly increases and increasingly shifts the peak resonant wavelength of the waveguide resonator.

Figure 8A:
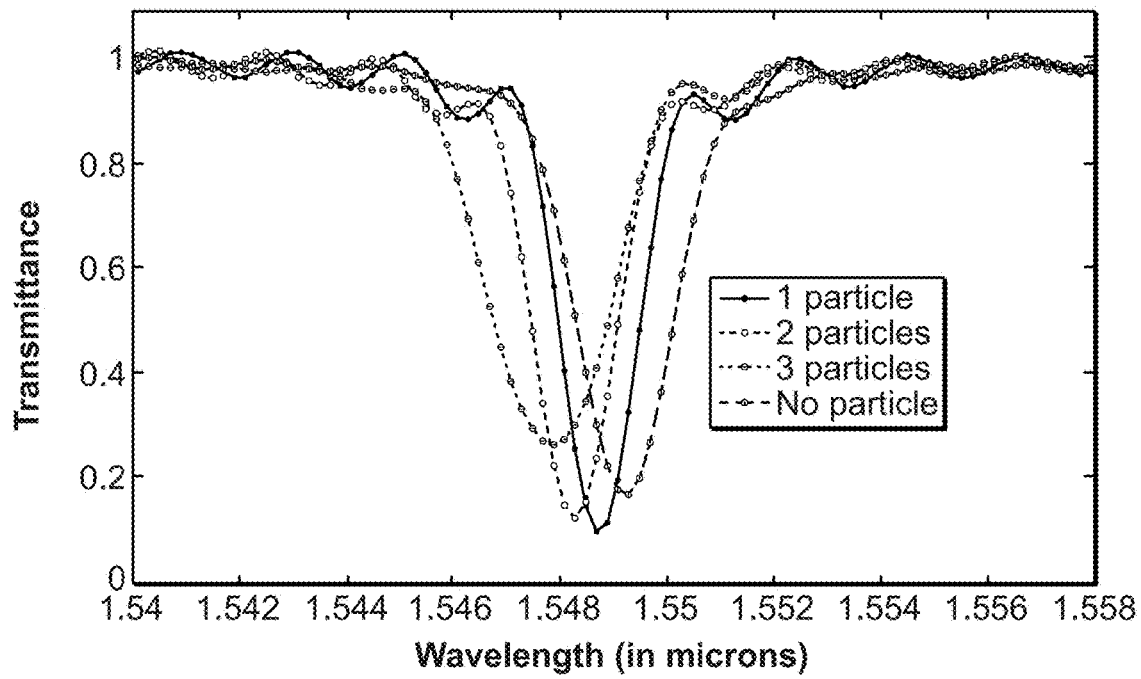
FIGS. 8A, 8B, and 8C are plots of simulated waveguide ring resonator transmittance as a function of wavelength when exposed to one aerosol particle, two aerosol particles, three aerosol particles, and with no exposure to aerosol particles, for aerosol particles of 100 nm-radius, aerosol particles of 200 nm-radius, and aerosol particles of 500 nm-radius, respectively.
Figure 8B:
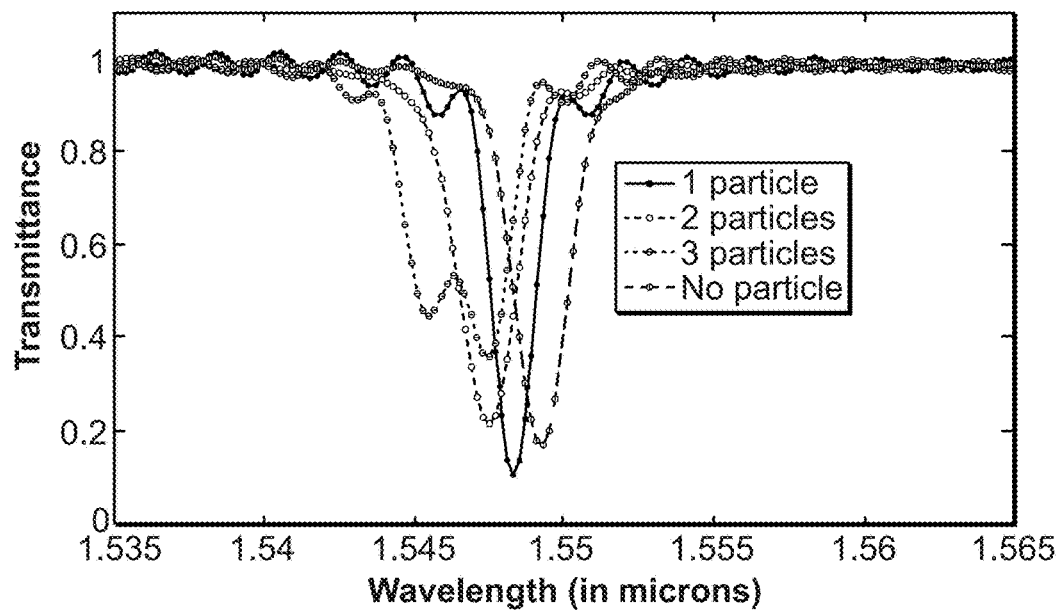
Figure 8C:
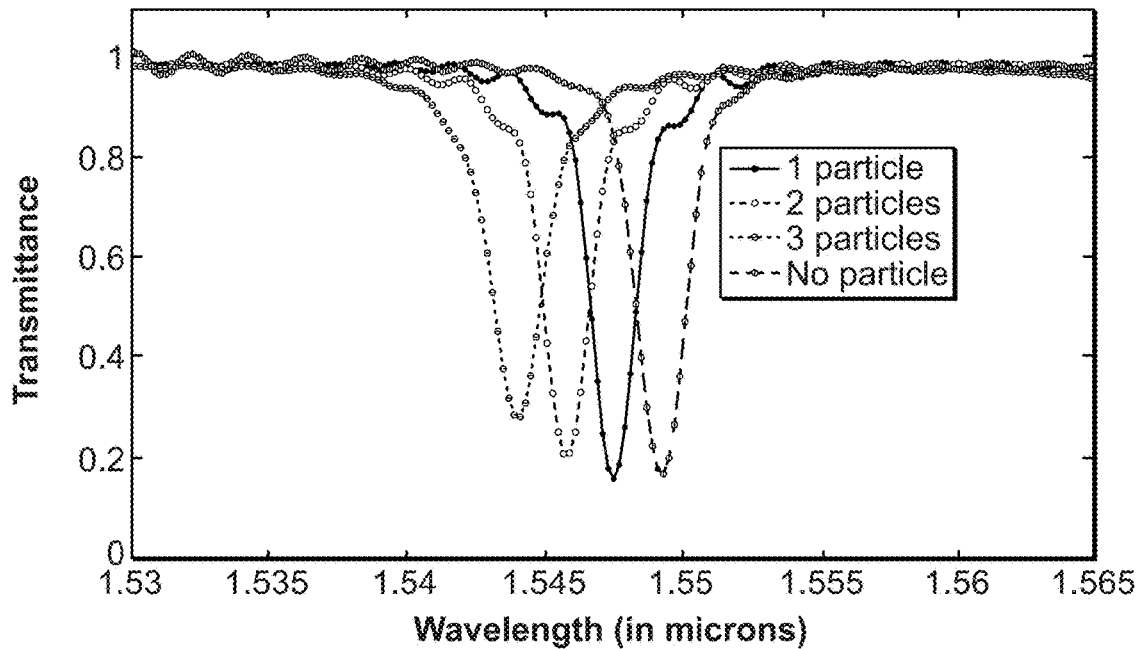
Figure 8D:
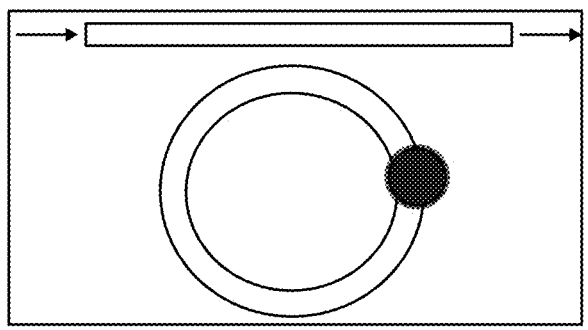
FIGS. 8D, 8E, and 8F are schematic planar views of a waveguide ring resonator configuration with one aerosol particle, two aerosol particles, and three aerosol particles, respectively, interacting with the resonator to produce the plotted data of FIGS. 8A, 8B, and 8C.
Figure 8E:
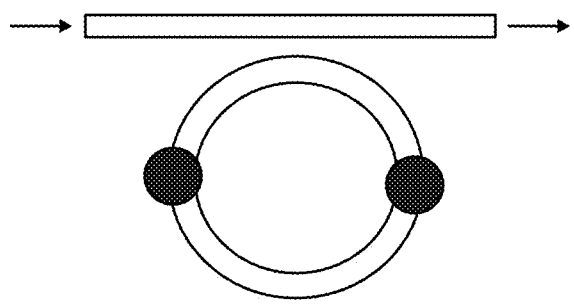
Figure 8F:
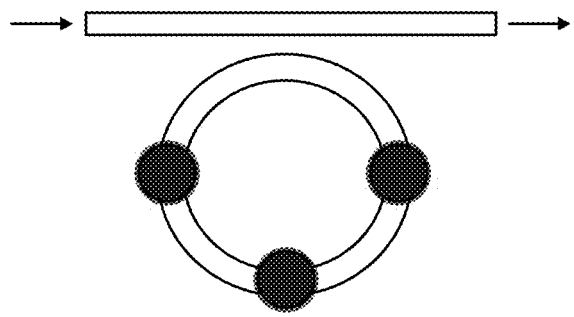

This is demonstrated quantitatively in the plots of FIGS. 8A-8C. Each of these FIGS. 8A-8C plots the optical transmittance of one ring waveguide resonator as a function of the wavelength of light propagating through the waveguide resonator, under conditions in which no particle is in the evanescent electric field of the resonator and under conditions in which 1, 2, or 3 particles are in the evanescent electric field of the resonator, for three different particle radii, namely, a 100 nm-particle radius, a 200 nm-particle radius, and a 500 nm-particle radius. This data is produced using a 2D finite difference time domain (FDTD) simulation, e.g., with a commercial simulation package such as FDTD Solutions, from Lumerical, Inc., Vancouver, BC, Canada. The waveguide ring resonator in this inquiry is modeled as a rectangular silicon nitride waveguide on a silicon dioxide-coated substrate in free space, with a rectangular waveguide that is 180 nm thick and 200 nm wide, having an inner ring radius of 2.9 microns and an outer ring radius of 3.1 microns; a coupling bus waveguide of 1 micron in width and 180 nm in thickness is here specified. FIGS. 8D-8F are schematic top-down views of the particle locations relative to the waveguide ring resonator that produce the results of the plots of FIGS. 8A-8C, respectively.

Figure 8G:
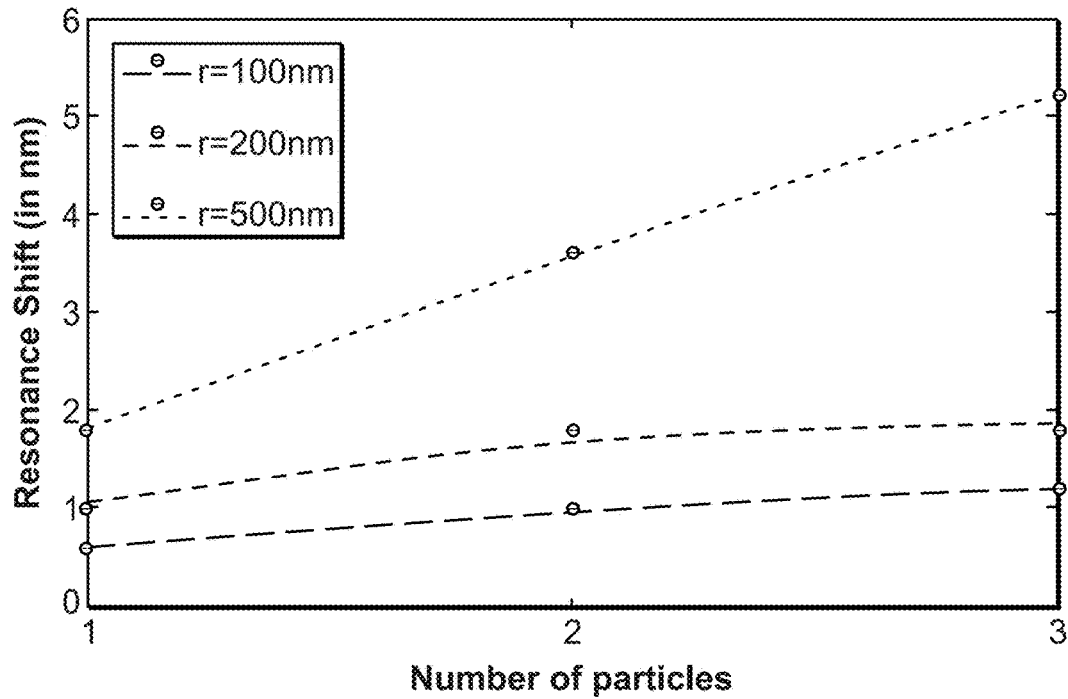
FIGS. 8G and 8H are plots of the shift in peak resonant wavelength of a waveguide ring resonator as a function of number of aerosol particles simulated to interact with the resonator for aerosol particle radii of 100 nm, 200 nm, and 500 nm, and as a function of radius of aerosol particles for one aerosol particle, two aerosol particles, and three aerosol particles simulated to interact with the resonator, respectively.
Figure 8H:
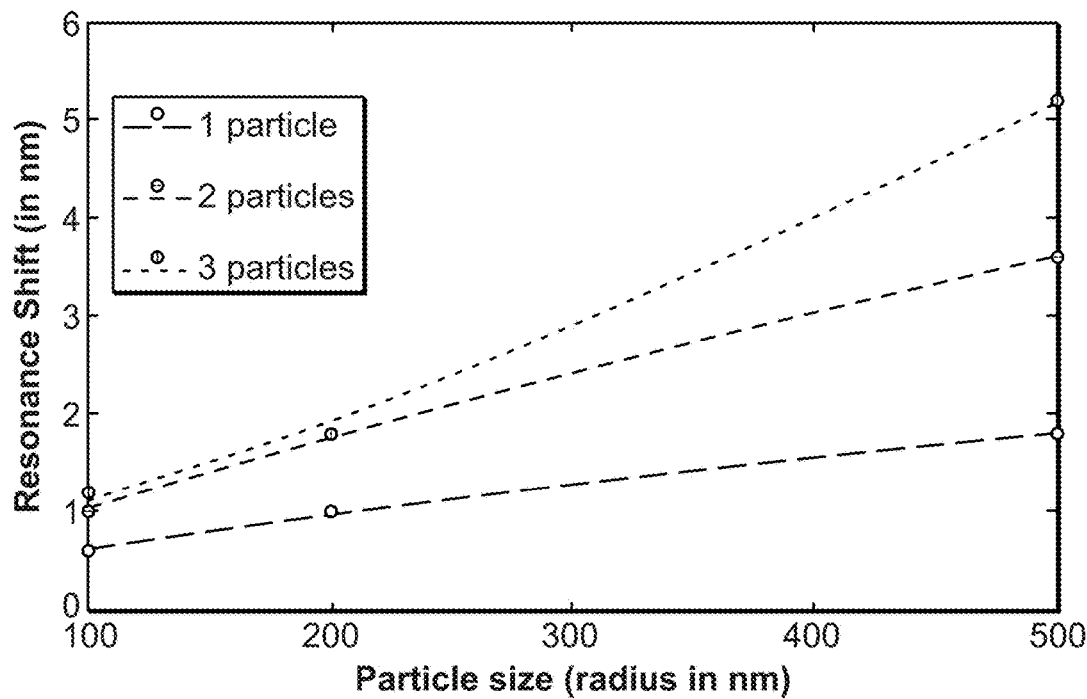
Figure 11:
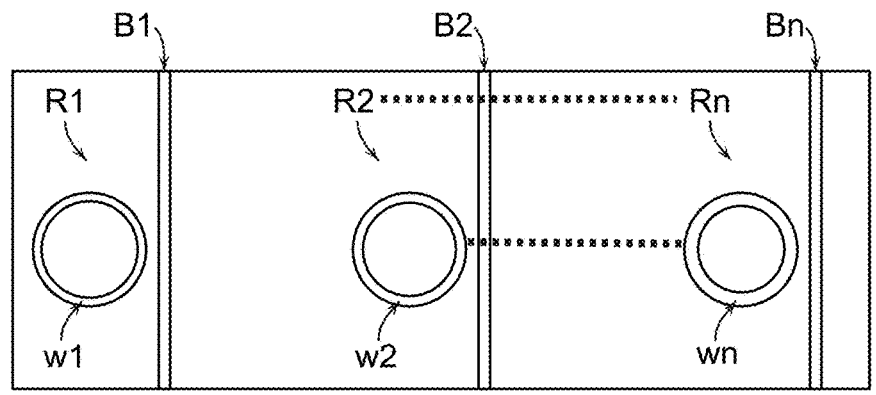
FIG. 11 is a schematic planar view of a set of n tandem waveguide ring resonators each having a separate waveguide coupling bus, the figure defining the geometric considerations for the set.
Figure 12:
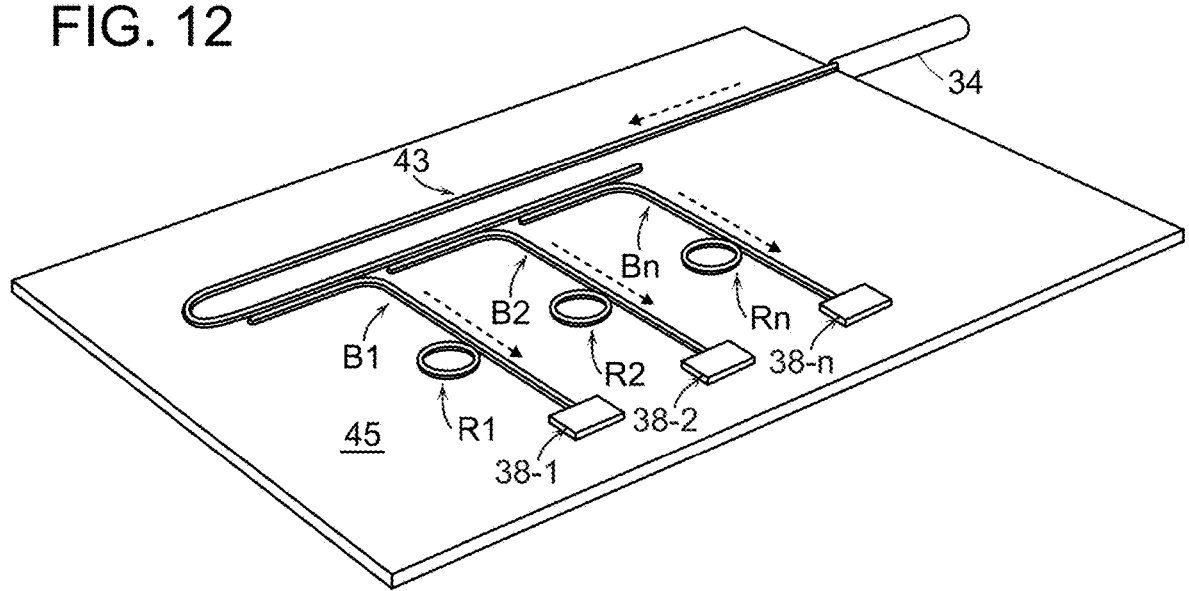
FIG. 12 is a schematic perspective view of a set of n tandem waveguide ring resonators, each of a different resonator waveguide width, all sharing a common input bus from a laser source, each ring resonator in communication with a separate coupling bus and in communication with a separate photodetector.
Figure 13:
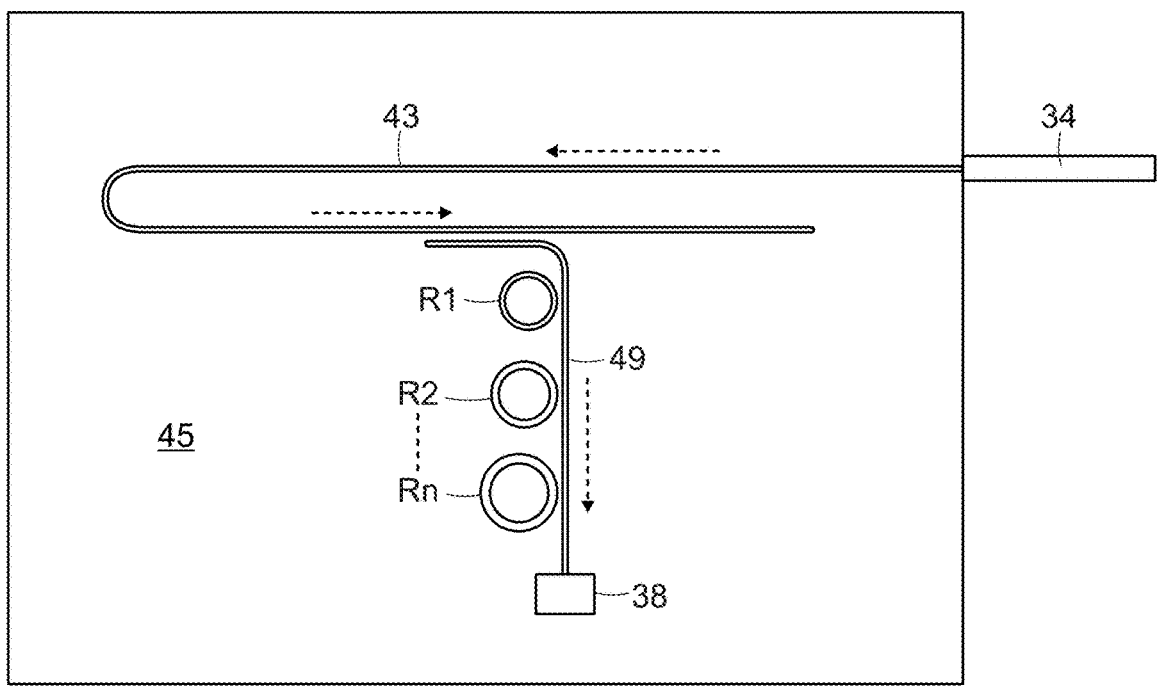
FIG. 13 is a schematic planar view of a set of n tandem waveguide ring resonators, each of a different resonator waveguide width, all sharing a common input bus from a laser source and all in communication with a common coupling bus and in communication with a common photodetector.

As seen in the plots of FIGS. 8A-8C, the shift in peak resonant wavelength of the waveguide resonator from a natural, baseline no-particle state becomes larger as the number of particles within the evanescent electric field is increased. The plots of FIGS. 8G and 8H represent this information as resonant peak shift as a function of number of particles, for different particle radii, and as a function of particle size, for different number of particles, respectively. The inventors herein have discovered that the shift in peak resonant wavelength can therefore be exploited to determine both particle size and number of particles that interact with the evanescent electric field of a waveguide resonator.

Accordingly, in one embodiment, there is configured an aerosol particle sensor including at least two tandem waveguide resonators, i.e., two or more separate, different waveguide resonators, each separate, different waveguide resonator having a different waveguide width but formed of the same material and having the same waveguide thickness. Each resonator in the set can have a different radius, but it can be preferred to provide the resonators with the same radius for ease of analysis, if in a ring shape, or to provide the same curve radius and straight section length, if in a racetrack shape. The condition of different waveguide width enables each of the at least two separate, different waveguide resonators to develop a different peak resonant wavelength shift in response to particles in the vicinity of the plurality of waveguide resonators, and together to provide a unique peak resonant wavelength shift identifier that is a function of particle size and particle number, as well as other particle characteristics, such as particle geometry.

There is no limit to the number of waveguide resonators that can be employed in tandem for particle sensing. In one embodiment, at least three or more separate, different waveguide resonators are employed in tandem in an aerosol particle sensor, each of the at least three or more separate different waveguide resonators having a different waveguide width. In one embodiment, at least four or more separate, different waveguide resonators are employed in tandem in an aerosol particle sensor, each of the at least four or more separate different waveguide resonators having a different waveguide width.

Referring to FIGS. 9A-9C, there are shown table maps that present values of the shift in peak resonant wavelength as a function of particle radius and as a function of particle number count, for a waveguide ring resonator of 700 nm in width, a waveguide ring resonator of 800 nm in width, and a waveguide ring resonator of 900 nm in width, respectively; each waveguide ring resonator is here a silicon nitride waveguide of 400 nm in thickness. Each of these maps cross-characterizes a waveguide resonator response across a population of particle sizes and particle number counts.

With the mapping shown in FIGS. 9A-9C for the peak resonant wavelength shift of each of three ring resonators across different particle radii and different numbers of particles, there results a unique signature set of peak resonant wavelength shifts for a given number count and size of a particle. In other words, for a given number of particles of a given particle size that interact with each waveguide resonator in a set of different waveguide resonators, there is a unique and corresponding set of peak resonant wavelength shift values $(RS_1, RS_2, \ldots, RS_n)$, where n is the number of waveguide resonators employed in the set of waveguide resonators and $RS_n$ is the resonant peak wavelength shift for the $n^{th}$ resonator.

In one embodiment for managing and analyzing this resonant wavelength shift data, referring also to FIG. 10, there is produced a set of peak resonant wavelength shift values for each waveguide resonator, for a range of particle radii over a range of particle number count. In the example mapping of FIG. 10, there are given the peak resonant wavelength shift, values for three different waveguide resonators, $R_1$, $R_2$, and $R_3$, for a number of particles between one and six, for a particle radius of 100 nm and again for a particle radius of 200 nm. This data is that of the first two columns of each of the mappings in FIGS. 9A-9C. With this 2D scattering map, a set of peak resonant wavelength shift values can be correlated to a specific number of particles and a specific particle size. For example, for the peak resonant wavelength shift value set of (0.1675, 0.2499, 0.2988) it is indicated that there exist 5 aerosol particles of about 200 nm in radius interacting with the three tandem waveguide resonators.

This mapping can be extended to any number of particles and any particle size that is within a range of interest; particle radii up to any selected radius, such as the 1000 nm particle radius included in the maps of FIGS. 9A-9C could be included in additional data sets in the map of FIG. 10. It is recognized that such a mapping can be produced by simulation methods, and by scattering or transmission matrix theory to produce a mathematical model that determines the values of such a mapping.

It is recognized herein and provided in further embodiments, that this mapping between particle size and particle number count for resonant peak wavelength shift values can be extended to characterization of other particle attributes, such as particle shape. For example, generally cylindrical, generally spherical, generally cubic, generally rectangular, and other shapes can be characterized for particle detection and analysis. The methodology is therefore not limited to a particular particle characteristic. This methodology can be extended in further embodiments to any number and geometry of waveguide resonators to produce a mapping, and corresponding data look-up-table, with unique sets of peak resonant wavelength shift values for a desired plurality of waveguide resonators that provide a signature of aerosol particle number count, particle size, and/or other characteristic of particles in the vicinity of the waveguide resonators.

Turning to embodiments for implementing tandem waveguide resonators in the aerosol sensor system provided herein, and referring to FIG. 11, in one example embodiment, there is arranged a first waveguide ring resonator, $R_1$, having a first resonator waveguide width, $w_1$, and a coupling bus waveguide $B_1$, for coupling light into/out of the first resonator $R_1$; and at least a second waveguide ring resonator, $R_2$, having a second resonator waveguide width, $w_2$, and a coupling bus waveguide $B_2$, for coupling light into/out of the second resonator $R_2$. More than two waveguide resonators can be included, up to a number, n, of resonators, with a waveguide resonator, $R_n$, having a resonator waveguide width, $w_n$, and a coupling bus waveguide $B_n$, for coupling light into/out of the $n^{th}$ resonator $R_n$. The width, $w_n$, of each resonator waveguide is different than the waveguide width of all other waveguide resonators in the set of resonators. The example shown in FIG. 11 shows ring resonators, but it is to be understood that waveguide racetrack resonators, or other resonator structure, can alternatively be implemented.

All of the tandem resonators in the set of n waveguide resonators can be microfabricated on separate platforms, or, in a particularly convenient embodiment shown in FIG. 12, can be microfabricated together on a common substrate 45. In this arrangement, a light source 34 can be provided off-substrate in the manner shown or alternatively, is microfabricated directly on the substrate with the set of n resonators. In one embodiment, a common input bus 43 directs light from the light source 34 to the location of individual and separate waveguide coupling buses $B_1$-$B_n$ that each deliver light to a corresponding waveguide resonator $R_1$-$R_n$. Light coupled from each resonator $R_1R_n$ back to each corresponding coupling bus $B_1$-$B_n$ is detected by a corresponding photodetector 38-1-38-*n* as shown in FIG. 12. With this arrangement, there is provided a set of n tandem waveguide resonators that can together provide data for ascertaining aerosol particle characteristics such as the size and number count of aerosol particles that are in the vicinity of the waveguide resonators. The number, n, of waveguide resonators to be included in the set of tandem resonators can be selected based on a desired degree of sensitivity, resolution of measurement, or other parameter, and is not limited to a particular number.

In a further embodiment, shown in FIG. 13, all of the tandem resonators in the set of $R_1$-$R_n$ of n waveguide resonators are microfabricated on a common substrate 45 and all n waveguide resonators share a common coupling bus 49. Here, a common input bus 43 directs light from the light source 34, which can be off-chip or monolithically integrated by microfabrication on-chip, to the location of the common coupling bus 49, and the set of $R_1$-$R_n$ waveguide resonators share the coupling bus 49. Light from each of the $R_1$-$R_n$ resonators is coupled out to the one coupling bus 49 and detected by one photodetector 38.

In a further embodiment, shown in FIG. 14, this configuration of a row of tandem resonators in FIG. 13 is extended to an array 47 of tandem resonators. Here, a light source 34, shown here integrated on-chip, delivers light into an input bus 43 that is arranged to couple light from the input bus 43 into each resonator in a row of multiplexer resonators, with each multiplexer resonator in the row being sized differently to couple light of a selected wavelength $m\lambda_1$, $m\lambda_2$, . . . , $m\lambda_m$, from the input bus 43 to a corresponding coupling row bus, $B_1$, $B_2$, . . . , $B_m$. Each coupling row bus, $B_1$, $B_2$, . . . $B_m$, in turn couples light to a number, n, of resonators that are arranged along a given coupling row bus. Each resonator 1-to-n disposed along a given coupling row bus has a common resonator radius, $r_m$, designated for the $m^{th}$ row. Each resonator that is in a given resonator column has a common waveguide width, $w_n$, designated for the $n^{th}$ column. Thus, there are in rows of n columns of resonators in the array 47 for a number, n×m, of resonators in the array. With this resonator array 47, there can be produced a 2D scattering map across wavelengths for sensing particle attributes such as particle size and particle number count.

Turning now to considerations for the selection of geometric parameters of tandem waveguide resonators in embodiments like those of FIGS. 12-14, it is to be recognized that in general, an operational wavelength range must first be selected to set the fundamental parameters of the resonator waveguides. The operational wavelength range can be selected based on, e.g., available light sources, available photodetectors, and even more importantly, based on the evanescent electric field extents desired to be produced by the resonators. Then, MODE simulations, such as FIMMWAVE, from Lumerical, Inc., Vancouver, BC, Canada, can be carried out, in the conventional manner, to set the desired waveguide geometry. For example, waveguide operation can be specified for the near IR spectral range of between about 1500 nm and about 1600 nm in wavelength, for the mid-IR spectral range of between about 3 microns and about 3.5 microns in wavelength, or for another selected spectral range.

A suitable rectangular waveguide cross section can be specified for a selected waveguide material selection. In one embodiment, the resonator waveguide is microfabricated with a suitable material, e.g., any material having a refractive index that is higher than the refractive index of the substrate material underlying the waveguide. Any optically transparent material having a refractive index larger than that of the underlying substrate material can be considered for fabrication of the waveguides. Example waveguide materials include silicon and silicon nitride or silicon dioxide, silicon carbide, germanium, $ZrO_2$—$TiO_2$, a chalcogenide glass, such as $Ge_{23}Sb_7S_{70}$, and $As_2Se_3$, Su-8, or other selected waveguide material disposed in rectangular form on a suitable substrate surface, e.g., a silicon dioxide-coated silicon wafer, on a mechanically flexible PDMS substrate, or other substrate, e.g., as taught in US Patent Application Publication No. 2007/0025410, published Feb. 1, 2007. Any suitable waveguide geometries can be employed in addition to rectangular. For example, rib-shaped, pedestal-shaped, or other waveguide geometries can be employed, as taught, for example, in U.S. Pat. No. 9,915,785, issued Mar. 13, 2018, hereby incorporated by reference in its entirety and as taught, for example, in U.S. Pat. No. 9,046,650, issued Jun. 2, 2015, hereby incorporated by reference in its entirety.

Based on a selected spectral range, MODE simulations can be conducted to set a selected waveguide thickness for the waveguide to support the necessary modes. In embodiments herein, it can be preferred that all of the tandem resonators, i.e., all resonators in a row, column, and array have the same waveguide thickness, so that all resonator waveguides can be microfabricated simultaneously on a common substrate. In embodiments herein, it can also be preferred that all resonators supporting a common wavelength range have a common effective radius, for ring resonators, and common curvature radius, for racetrack resonators.

In one design paradigm, there is selected the smallest waveguide width in a set of tandem resonator waveguides based on the lowest wavelength of a spectral range of interest, so that the diagonal of the smallest rectangular waveguide cross section is at least at large as one-half the lowest wavelength in the spectral range of interest. Given a selected waveguide thickness, the smallest resonator waveguide width can then be selected. For example, given a waveguide thickness of about 400 nm and given a wavelength of 1500 nm at the low end of the near-IR spectral range, then a minimum resonator waveguide width of about 635 nm would be prescribed.

Figure 15A:
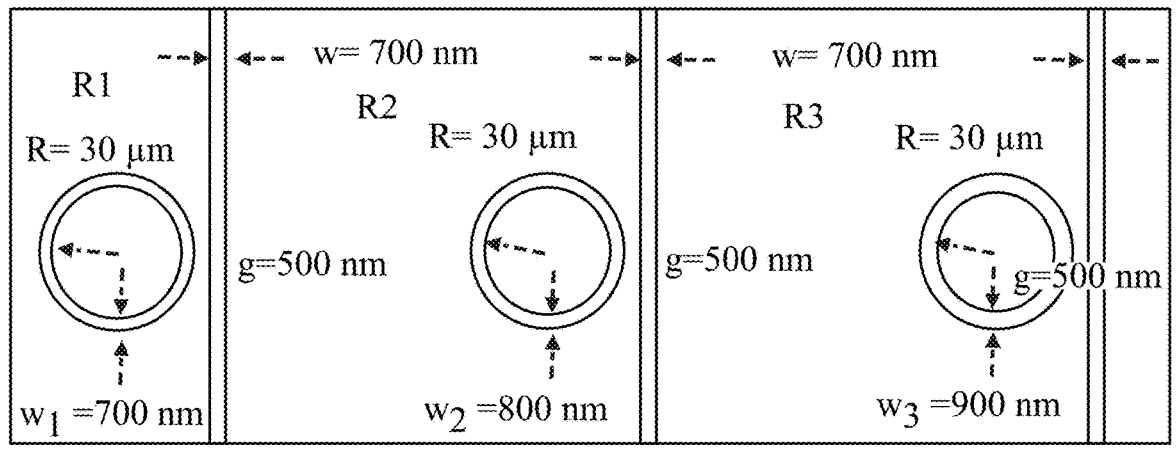
FIG. 15A is a schematic planar view of example geometric values for the ring resonators, coupling buses, and resonator-coupling bus gaps, for tandem set of waveguide ring resonators in the embodiment of FIG. 12, with n=3 for operation in a spectral range of near-IR wavelengths.
Figure 15B:
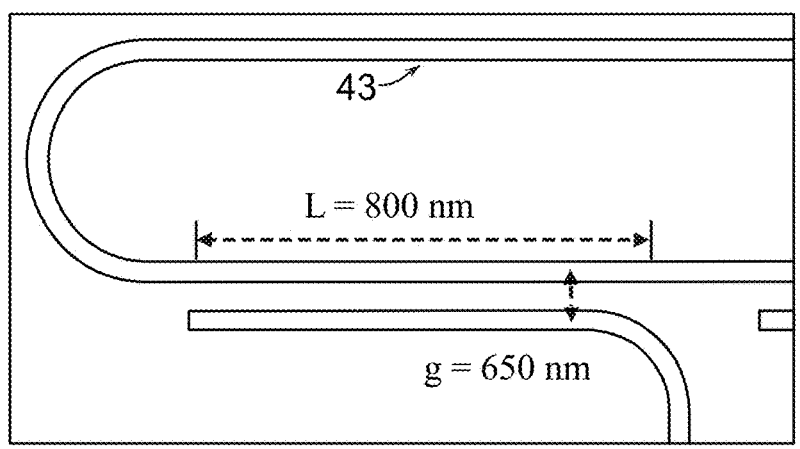
FIG. 15B is a schematic planar view of example geometric values for the coupling length between the input bus and each coupling bus, and the gap between the input bus and each coupling bus, for the geometric values given in FIG. 15A.

FIG. 15A presents the geometric values for an example set of three tandem ring resonators, $R_1$, $R_2$, and $R_3$, for a silicon nitride waveguide material, specified for operation in the near-IR spectral range of between about 1500 nm and about 1600 nm in wavelength. FIG. 15B shows that for this design, there can be a coupling length of about 800 nm and a coupling gap of about 650 nm between the input bus 43 and each coupling bus $B_1$, $B_2$, and $B_3$. FIG. 15C is a table presenting this data. In this example, the three ring resonators each have a thickness of 400 nm and a ring radius of 50 microns. The three coupling bus waveguides, $B_1$, $B_2$, and $B_3$ are all 700 nm wide, and the center-to-center gap between each bus waveguide and corresponding ring resonator waveguide is 500 nm. The width, $w_1$, of the first ring resonator waveguide is 700 nm; the width, $w_2$, of the second ring resonator waveguide is 800 nm; and the width, $w_3$, of the third ring resonator waveguide is 900 nm. FIG. 15D is a table of an additional, different example embodiment of geometric values for the three ring resonators. Here each resonator ring has a different radius as well as a different waveguide width.

Figure 16A:
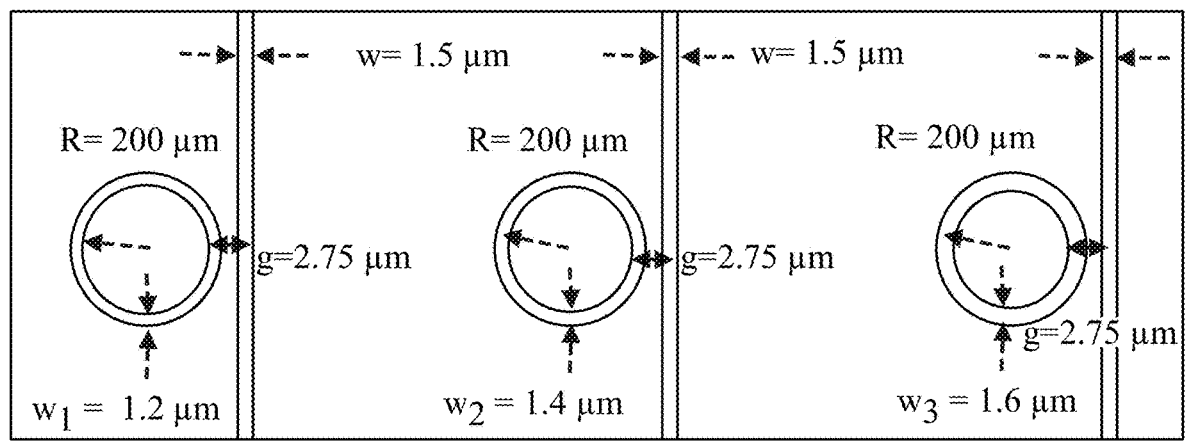
FIG. 16A is a schematic planar view of example geometric values for the ring resonators, coupling buses, and resonator-coupling bus gaps, for tandem set of waveguide ring resonators in the embodiment of FIG. 12, with n=3, for operation in a spectral range of mid-IR wavelengths.
Figure 16B:
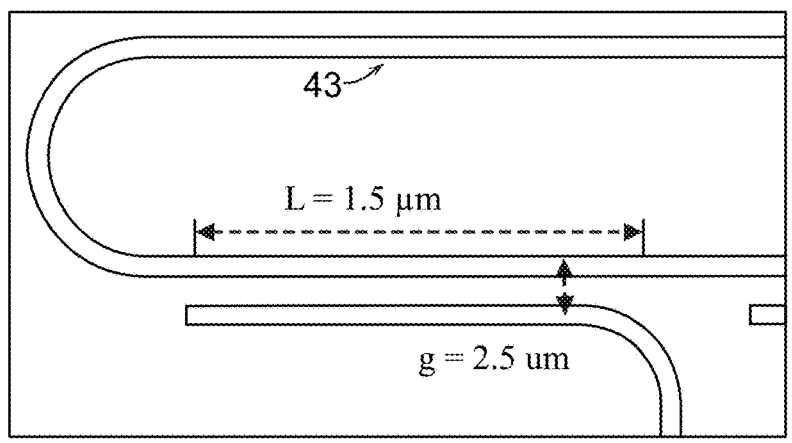
FIG. 16B is a schematic planar view of example geometric values for the coupling length between the input bus and each coupling bus, and the gap between the input bus and each coupling bus, for the geometric values given in FIG. 16A.

FIG. 16A presents the geometric values for an example set of three tandem ring resonators, $R_1$, $R_2$, and $R_3$, for a chalcogenide waveguide material, specified for operation in the mid-IR spectral range of between about 3.0 microns and about 3.4 microns in wavelength. FIG. 16B shows that for this design, there can be a coupling length of about 1.5 microns and a coupling gap of about 2.5 microns between the input bus 43 and each coupling bus $B_1$, $B_2$, and $B_3$. FIG. 16C is a table presenting this data. In this example, the three ring resonators each have a thickness of 1.2 microns and a ring radius of 200 microns. The three coupling bus waveguides, $B_1$, $B_2$, and $B_3$ are all 1.5 microns-wide, and the center-to-center gap between each bus waveguide and corresponding ring resonator waveguide is 2.75 microns. The width, $w_1$, of the first ring resonator waveguide is 1.2 microns; the width, $w_2$, of the second ring resonator waveguide is 1.4 microns; and the width, $w_3$, of the third ring resonator waveguide is 1.6 microns.

Figure 14:
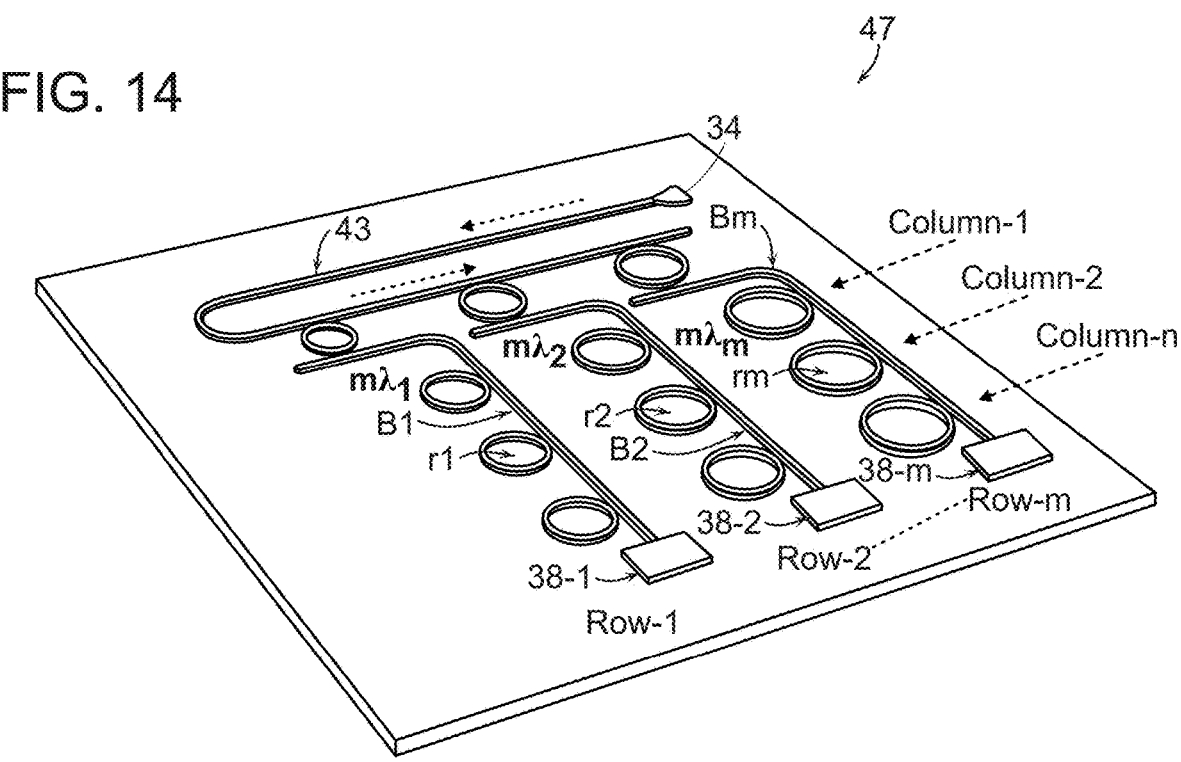
FIG. 14 is a schematic perspective view of an array of n columns of m rows of tandem waveguide ring resonators, each resonator in a given row of a different resonator waveguide width, all sharing a common input bus from a laser source and each row having a separate coupling bus of a distinct wavelength set by a multiplexer resonator in communication with the common input bus and the separate coupling bus, and each row in communication with separate photodetector.

In the design of a waveguide resonator array, as in the example embodiment shown in FIG. 14, the geometric specifications given in FIGS. 15A-15C and 16A-16C can be employed separately for each of three rows of resonators. The radius, $r_m$, of the ring resonators in each row, $r_1$, $r_2$, and $r_3$, is different from that of the other rows. All resonators in one row support a multiple of the wavelength $m\lambda_m$, and $m\lambda_1 < m\lambda_2 < m\lambda_3$ across the array rows. With this relation, the ring radius for each row is given as $r_1 = \lambda_1/2\pi n_{eff}$, $r_2 = \lambda_2/2\pi n_{eff}$, and $r_3 = \lambda_3/2\pi n_{eff}$, where $n_{eff}$ is the refractive index of the waveguide material. In one example of this design, for operation over the near IR spectral wavelength of between about 1500 nm and about 1600 nm, the three radii can be set as $r_1 = 30$ microns, $r_2 = 40$ microns, and $r_3 = 50$ microns.

With these example embodiments and geometric parameters, it is shown that there can be designed a tandem set of waveguide resonators that together enable sensing of characteristics of aerosol particles, such as aerosol particle size and particle number count analysis. The example geometric specifications given in FIGS. 15A-D and FIGS. 16A-C are directed to sets of three tandem waveguide resonators, for clarity, but it is to be recognized that any number in a plurality of tandem waveguide resonators can be employed; in other words, the number, n, of waveguide resonators to be included is two or more, so that n≥2.

In further embodiments provided herein, the response of one or more waveguide resonators in a tandem set of waveguide resonators is employed to determine the chemistry of aerosol particles in the vicinity of the resonator. As a result, the particle characteristics of particle chemistry, particle size, and particle number count are all determined by the tandem waveguide resonator arrangements provided herein, along with other selected particle characteristics such as particle geometry.

In one embodiment, particle chemistry is indicated by changes in the quality factor, Q, of the peak in resonance of a waveguide resonator. The quality factor, Q, of a resonance peak is degraded from a baseline, ideal condition by fluctuations in temperature, waveguide roughness, and mechanical pressure within the waveguide of a resonator, as well as by absorption losses from the waveguide and/or other materials, such as particles, that are in the evanescent electric field in the vicinity of the waveguide. With temperature and pressure fluctuations kept in strict control, changes in the quality factor of a resonator peak are due substantially entirely to optical energy absorption by particles in the waveguide resonator vicinity. It is well understood that the optical energy absorption of materials is material-specific, and therefore provides a unique signature for chemical bonds in the material of a particle.

Figure 17A:
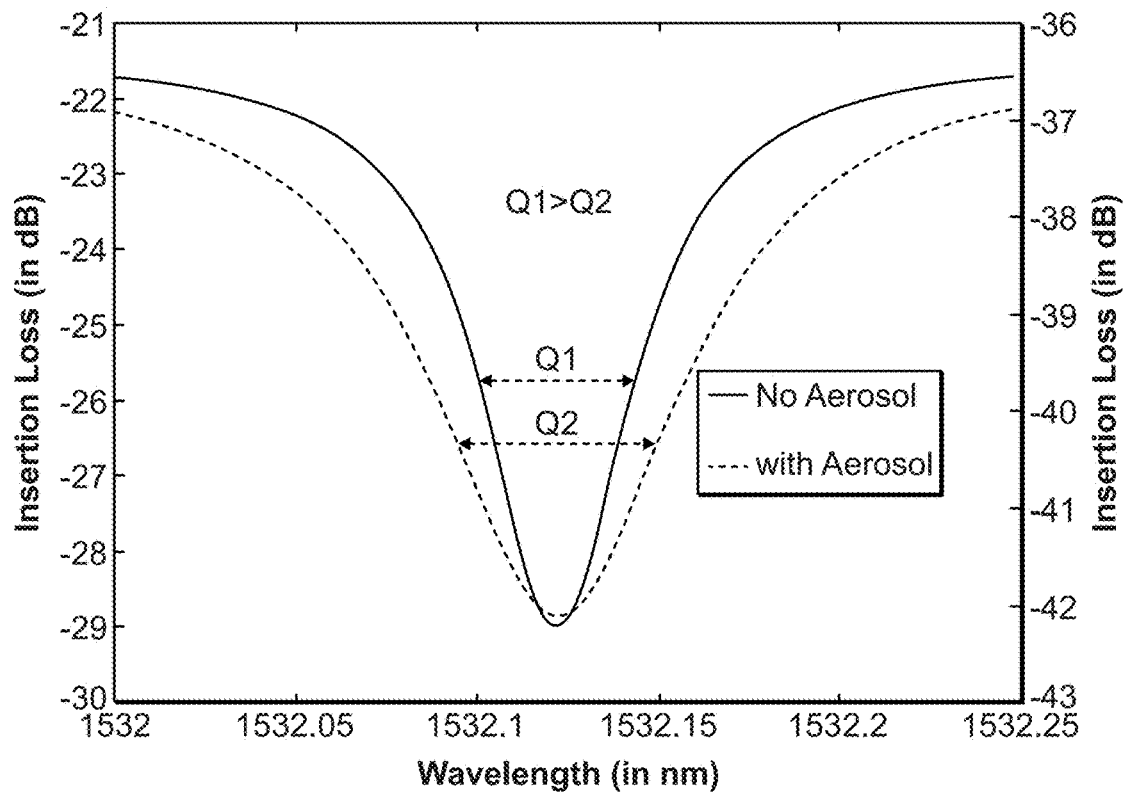
FIGS. 17A and 17B are plots of the insertion loss of a waveguide ring resonator as a function of wavelength for conditions of resonator exposure to aerosol particles and non-exposure to aerosol particles, for wavelengths at which aerosol particles absorb energy from the waveguide resonator evanescent electric field and for wavelengths at which a population of aerosol particles 12, into the system and to sense characteristics of the aerosol particles 12, here to produce an output indication 14 of aerosol particle number count and/or to produce an output indication 16 of aerosol particle size, and to produce an output indication 22 of aerosol particle chemistry. The characterized aerosol particles are output of the aerosol sensor system 20 as an aerosol output 18. This demonstrates that any with the light in the ring after every circulation around the ring and optical power in the ring builds to a steady state.
Figure 17B:
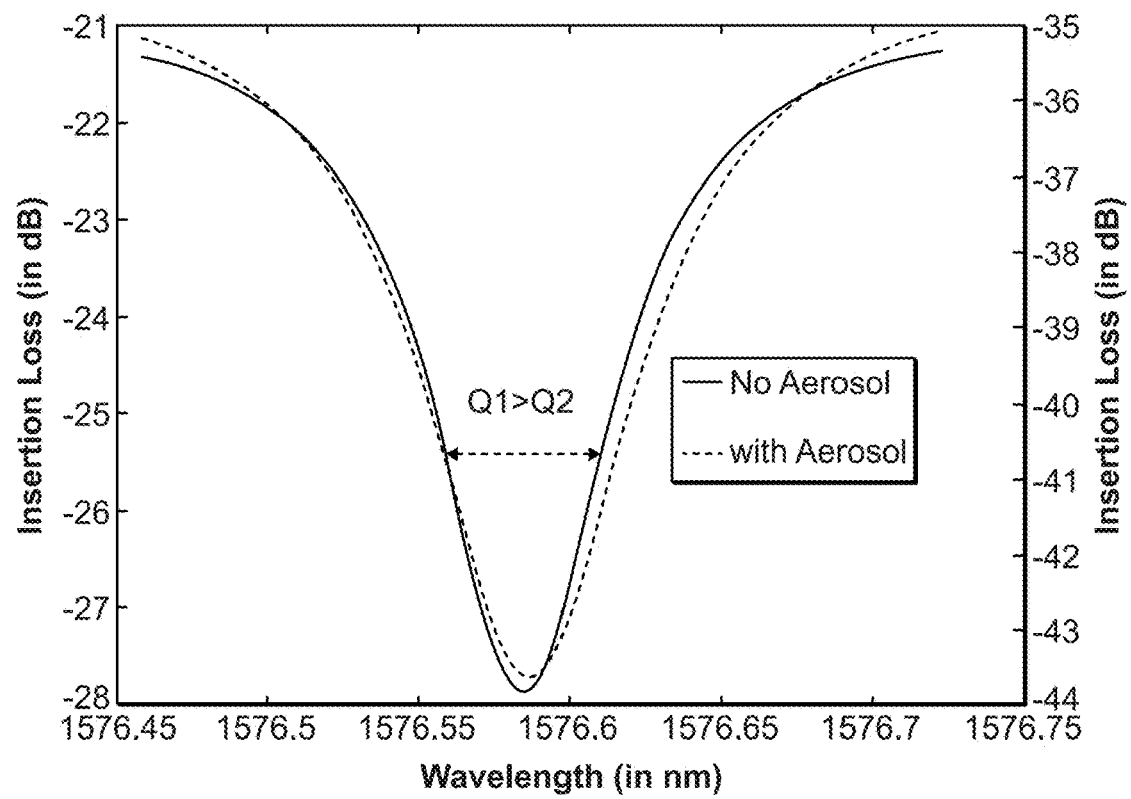

The plots of FIGS. 17A-17B illustrate this condition of optical energy absorption by particles in the vicinity of a waveguide resonator. FIG. 17A shows a plot of waveguide resonant frequency in the absence of particles in the vicinity of a waveguide resonator and shows a plot of waveguide resonant frequency at an input wavelength at which aerosol particles are absorbing. The quality factor, $Q_1$, of the resonance peak in the absence of absorbing particles is shown to be much greater than the quality factor, $Q_2$, of the resonance peak in the presence of absorbing particles. FIG. 17B shows a plot of waveguide resonant frequency in the absence of particles in the vicinity of a waveguide resonator, and shows a plot of waveguide resonant frequency at an input wavelength at which aerosol particles are present but not absorbing. The quality factor, $Q_1$, of the resonance peak in the absence of absorbing particles is shown here to be substantially identical to the quality factor, $Q_2$, of the resonance peak in the presence of non-absorbing particles; no difference in quality factor results. This data determined from the transmission spectrum measured across a selected spectral range.

In one example, for which the data of FIGS. 17A-17B was produced, a steady state flow rate of 250 particles/cm$^3$ of an N-methyl aniline aerosol was delivered for 120 s to one SiN waveguide racetrack resonator of 800 nm in width and 50 microns in radius, having a 50 micron-long straight length coupling region, 800 nm-wide coupling bus, 900 nm-wide coupling bus-to-racetrack gap.

Figure 17C:
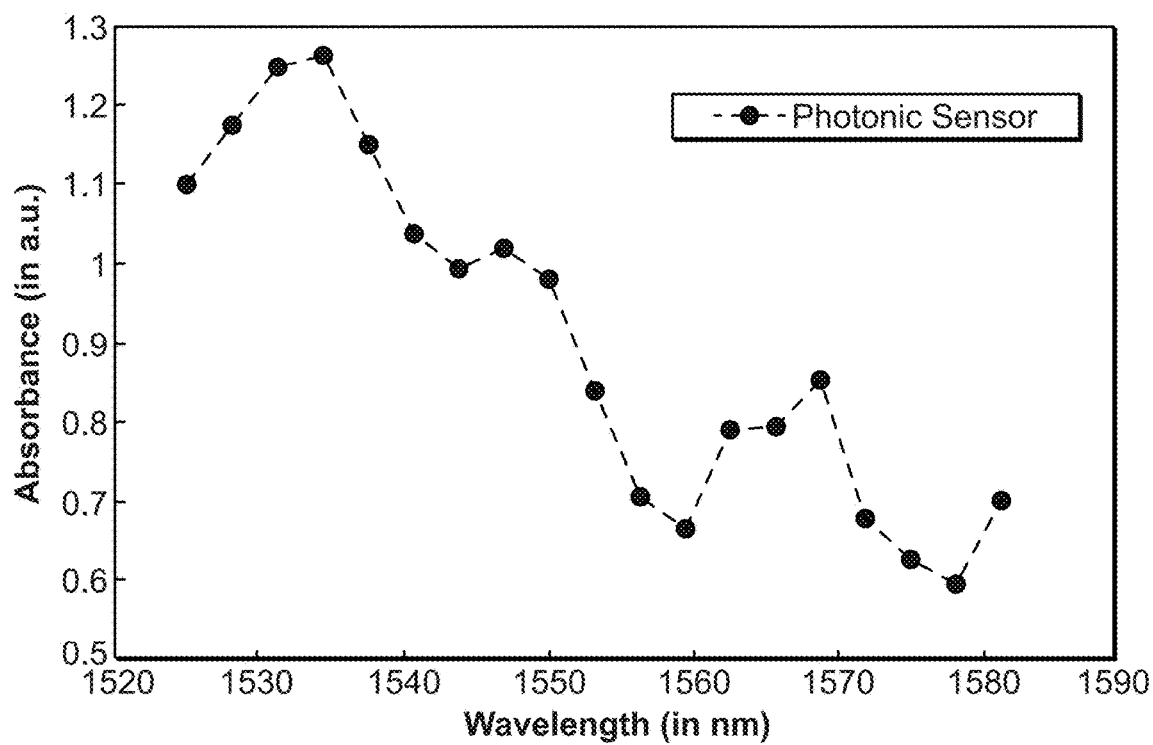

Thus, a determination of absorbing particle chemical bonds is indicated by changes in quality factor, which is a wavelength-dependent parameter. By analyzing the quality factor, Q, of all resonant peaks across a selected spectral range of wavelengths, the aerosol particle absorbance at each wavelength can be determined. Then the absorption spectra of a particle can be mapped and correlated to the corresponding chemical bonds indicative of the absorption spectra. FIG. 17C is an example of the determined absorption spectra for the N-methyl aniline aerosol that produced the data of FIGS. 17A-17B. This spectra is the chemical absorbance signature for N-methyl aniline and can be verified by reference to public data, such as NIST absorbance spectra data.

One or more waveguide resonators in a set, row, column, or entire array of waveguide resonators can be employed to provide data that is indicative of particle chemistry. Thus, the tandem sets of waveguide resonators shown in FIGS. 12-16 are all particle chemistry sensors as well as particle size and particle number count sensors. A highly compact and portable aerosol sensor with full physio-chemical sensing capability is therefore provided.

Figure 18A:
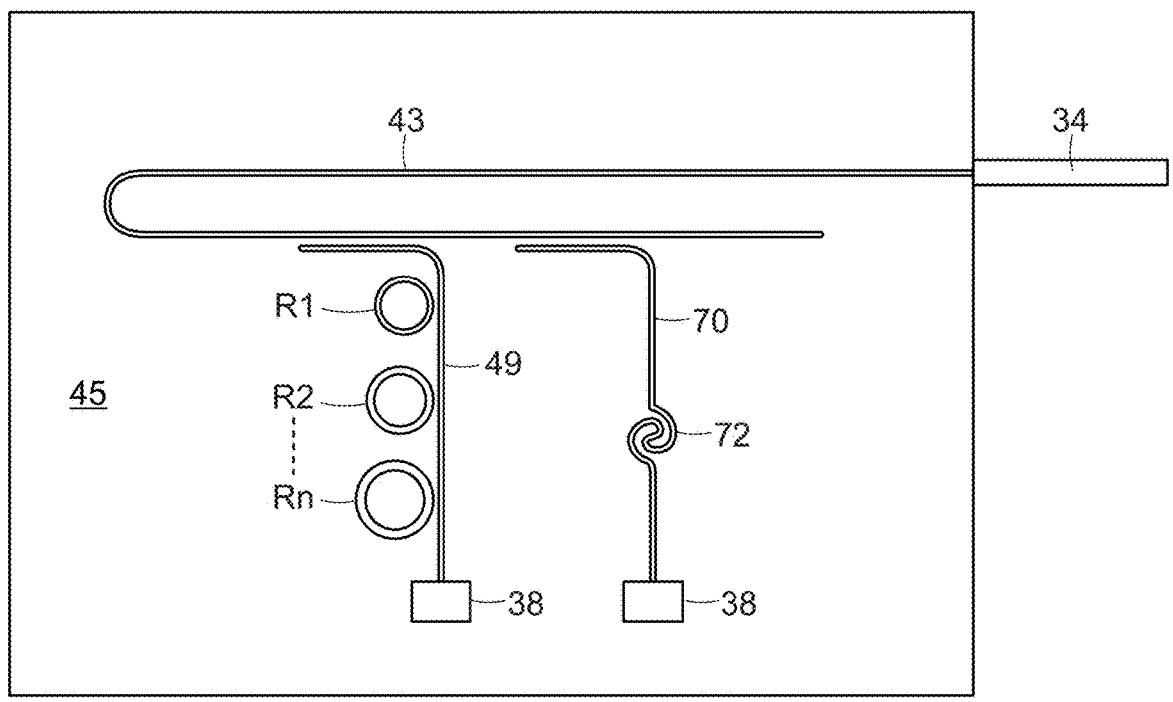
Figure 18B:
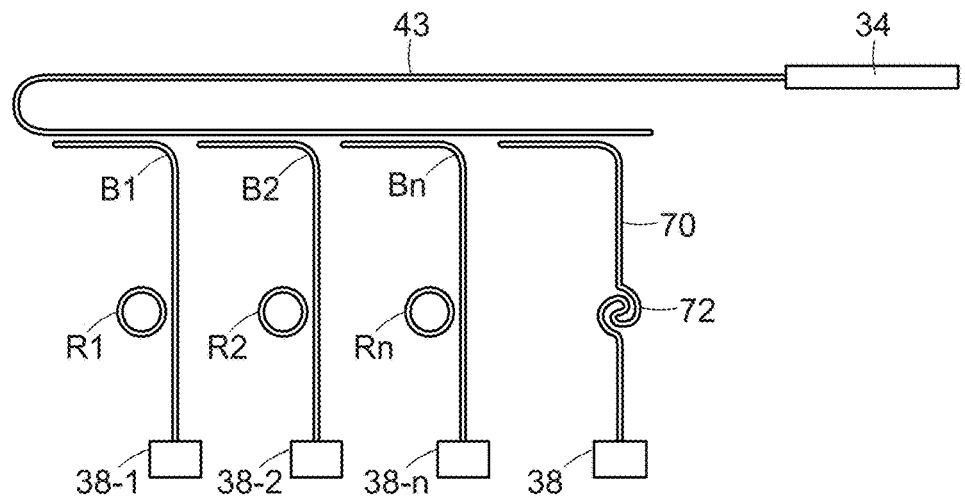

In further aerosol particle sensor embodiments provided herein, there is included, along with a tandem set of waveguide resonators, at least one non-resonant waveguide structure that is provided for determining a particle characteristic such as the chemistry of aerosol particles. Referring to FIGS. 18A-18B, in these embodiments, there is included in the particle sensor a plurality of tandem waveguide resonators, each of a different waveguide width, for determining particle size and/or particle count. As shown in FIG. 18A, the set of waveguide resonators can share a common coupling bus 49, or alternatively, as shown in FIG. 18B, each waveguide resonator can be disposed adjacent to a different bus, $B_1, B_2, \ldots, B_n$.

In either scenario, there is included an additional waveguide 70 that includes a waveguide length, including a waveguide path configured as-desired, such as in a spiral 72, for sensing the chemistry of particles in the vicinity of the waveguide 70, 72. An output detector 38 is provided for this additional waveguide 70. The waveguide spiral 72 shown in FIGS. 18A-18B is one example of a waveguide path that maximizes waveguide length in a given area for maximizing optical interaction of particles with the evanescent electric field in the vicinity of the waveguide, but is not limiting; other waveguide path geometries can be employed, such as paperclip paths, or other path that maximizes the ratio of waveguide perimeter/waveguide area.

To determine particle chemistry with the waveguide structure 70, 72, the broadband transmittance of the waveguide 70, 72 across a selected spectral range is measured without the presence of aerosol particles, and then this baseline transmittance is compared with the broadband transmittance spectrum of the waveguide, measured in the presence of aerosol particles. The corresponding absorption spectrum of the aerosol particles can then be known, and correlated to a chemical constituency with an absorption spectrum signature known for that chemistry absorption spectrum.

In the design of a waveguide structure 70, 72 for determining particle chemistry, in preferred embodiments the waveguide structure 70, 72 is a rectangular waveguide having a thickness that matches the thickness of other waveguide structures in the aerosol sensor, e.g., the thickness of input and coupling bus waveguides, and the set of waveguide resonators, so that all of the structures can be microfabricated simultaneously on a common substrate. Given the thickness of the waveguide, then the width of the waveguide is determined along with a selected waveguide path length.

In one embodiment, the waveguide is designed to support the TE and TM mode of optical propagation. Use simulation tools and methodology in the manner described above, the waveguide width is determined, to support the first two optical modes, as described in "Towards On-Chip Mid Infrared Photonic Aerosol Spectroscopy," Appl. Phys. Lett., 113, 231107, 2018, the entirety of which is hereby incorporated by reference. The waveguide loss is determined and based on desired sensitivity, a total waveguide length is selected.

In one example design for this embodiment, directed to mid-IR wavelengths of transmission for particle sensing, a waveguide of chalcogenide glass, e.g., $Ge_{23}Sb_7S_{70}$, is employed with a waveguide thickness of 1.2 microns, to match the waveguide thickness of the mid-IR tandem resonator design specification shown in FIG. 16C. The width of waveguide 70, 72 is then given as 1.5 microns, and the total length of the waveguide 70, 72, is about 1 cm. In one example design for this embodiment, directed to near-IR wavelengths of transmission for particle sensing, a waveguide of, e.g., silicon nitride is employed with a waveguide thickness of 400 nm, to match the waveguide thickness of the near-IR tandem resonator design specification shown in FIG. 15C. The width of waveguide 70, 72 is then given as 800 nm.

Figure 18C:
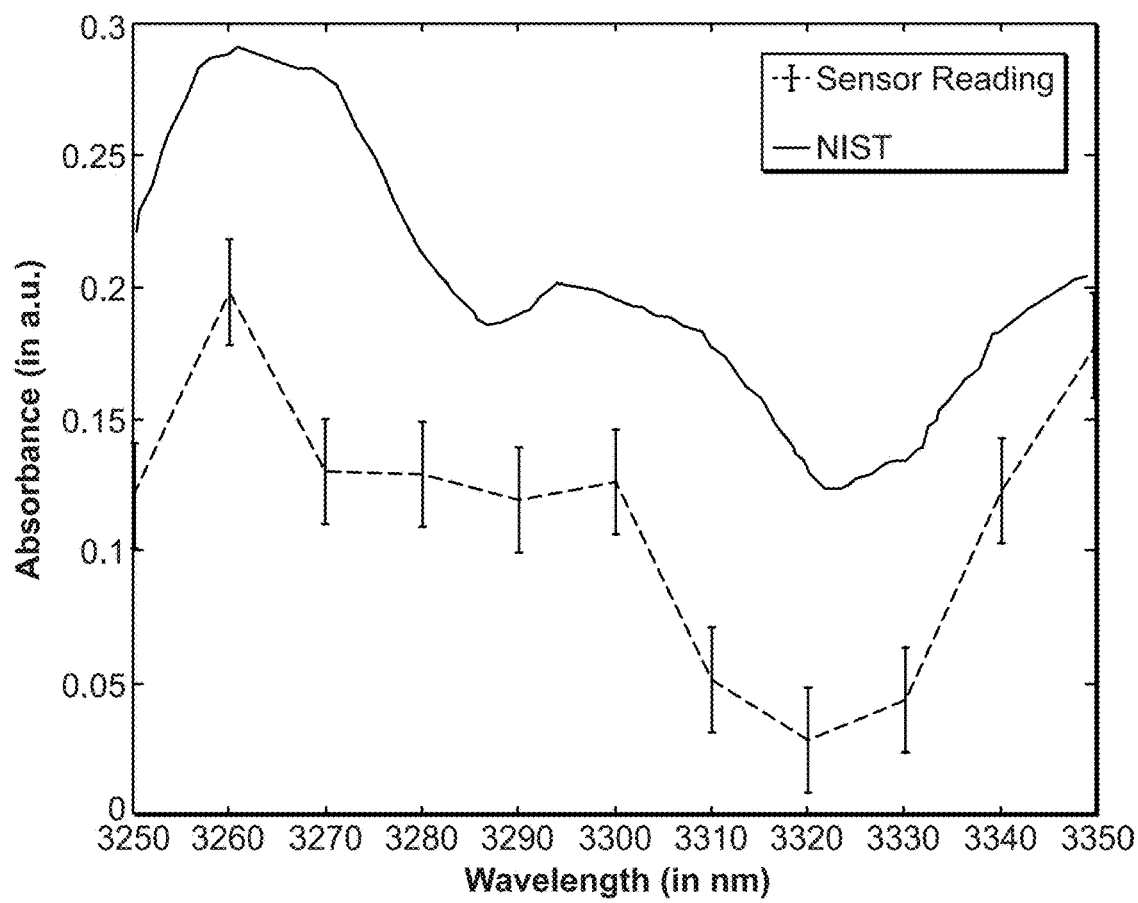

FIG. 18C is a plot of the absorption spectra for N-methyl aniline determined for the mid-IR specifications given just above, for an aerosol flow rate of between about 500 particles/area-s and about 1000 particles/area-s, along with the corresponding NIST reference spectra for N-methyl aniline, demonstrating good agreement between the two.

Turning to example embodiments for microfabrication of aerosol particle sensing arrangements provided herein, and referring to FIGS. 19A-19I, in one example microfabrication process 80 for waveguide particle sensor structures operating in the near-IR spectral region, a microfabrication substrate, such as a silicon substrate 82, single-side polished, is oxidized to produce a 3 micron-thick layer of silicon dioxide 84 on the substrate surface as shown in FIG. 19A. Referring to FIG. 19B, low pressure chemical vapor deposition (LPCVD) is then conducted to produce a layer of silicon nitride ($Si_3N_4$) on the oxide layer, to form the waveguide material. The thickness of the silicon nitride layer sets the thickness of the waveguide structures to be included, and therefore is set appropriately, e.g., in one example, at 400 nm. This step produces the waveguide material layer 86 shown in FIG. 19C. An appropriate lithographic process, such as e-beam lithography, is then conducted, as specified in FIG. 19D, with a selected photoresist to impart selected waveguide widths to the waveguide structures. In one example process, a layer of high-resolution negative e-beam resist 88, shown in FIG. 19E, produced as a coating of, e.g., about 300 nm in thickness, is formed, e.g., by first spinning at 500 rpm for 6 s and then spinning at 3000 rpm, for 30 s, with a subsequent bake for 1 min at 90° C. E-beam lithography can be conducted in the conventional manner, e.g., a beam current of 20 nA with a dose of 400 microCoulomb/$cm^2$. The pattern is developed in the conventional manner.

Then, as specified in FIG. 19F, an appropriate pattern transfer process, such as reactive ion etching (RIE), is conducted to transfer the photoresist pattern to the silicon nitride waveguide layer, to form a patterned silicon nitride layer 90 as shown in FIG. 19G; the patterning etch is conducted with, e.g., $CF_4$ and $CHF_3$ plasma etching gases. As specified in FIG. 19H the photoresist layer is then removed, producing, as shown in FIG. 19I, patterned and fully exposed waveguide structures 92, the cross-section of one of which is shown.

FIGS. 20A-20D are cross-sectional views of steps in a microfabrication process 100 for waveguide particle sensor structures operating in the mid-IR spectral region. In a first step, a suitable substrate, such as a silicon wafer, not shown for clarity, is oxidized to form a thermal $SiO_2$ layer 102 on the substrate. Then a double layer liftoff process employing an undercut layer is conducted. For example, as shown in FIG. 20A, an undercut layer 104, e.g., a layer of PMGI of 1.5 microns in thickness, from MicroChem, Westborough, Mass., and an e-beam resist layer 106, e.g., a layer of ZEP-520A from ZEON CHEMICALS, LP, of Louisville, Ky., of 400 nm in thickness, are formed on the thermal silicon dioxide layer 102.

Turning to FIG. 20B, e-beam lithography is conducted on the resist and undercut layers to form an opening 108 that defines the waveguide structure to be formed. Then as shown in FIG. 20C, a layer 110 of selected waveguide material, e.g., the chalcogenide $Ge_{23}Sb_7S_{70}$ (GSS) is deposited, e.g., by thermal evaporation. The resist double layer structure is then lifted off in a conventional lift-off process, e.g., with N-methyl1-2-pyrrolidone, producing fully formed and exposed waveguide structures 112 as shown in FIG. 20D.

This chalcogenide-based waveguide fabrication, and the nitride-based microfabrication embodiment described above, can be extended for production of monolithic laser sources, optical multiplexers and buses, photodiode photodetectors, processing devices, other system componentry, and no particular fabrication or assembly process is required.

Figure 1A:
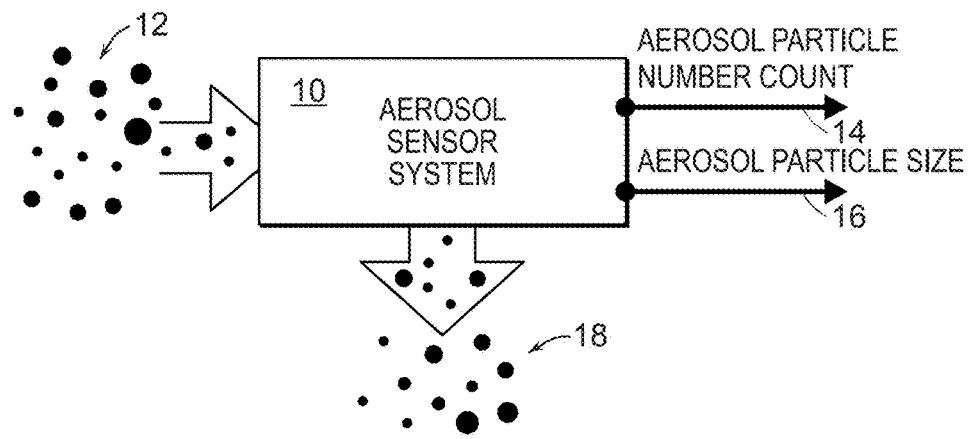
FIG. 1A is a schematic block diagram of a first aerosol sensor system embodiment, including system inputs and outputs.
Figure 1B:
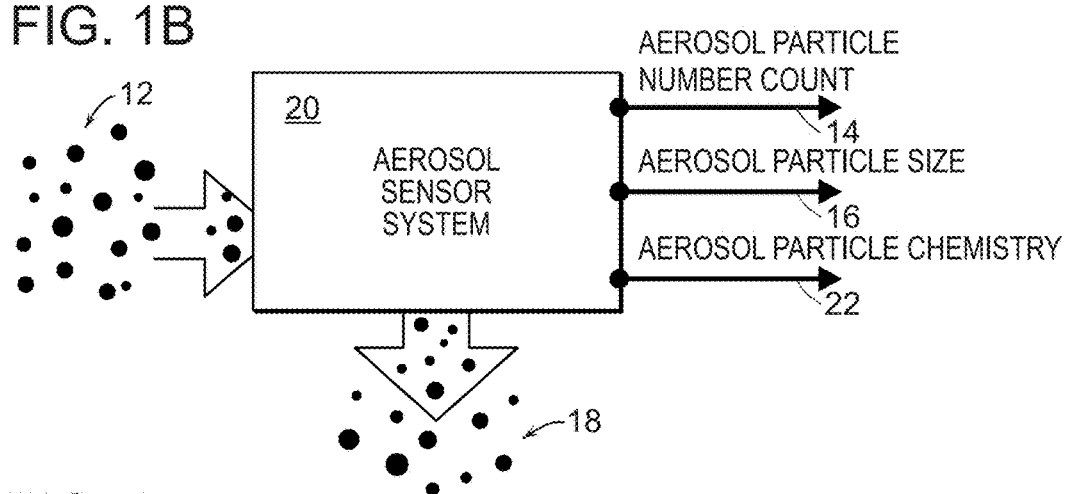
FIG. 1B is a schematic block diagram of a second aerosol sensor system embodiment, including system inputs and outputs.
Figure 2:
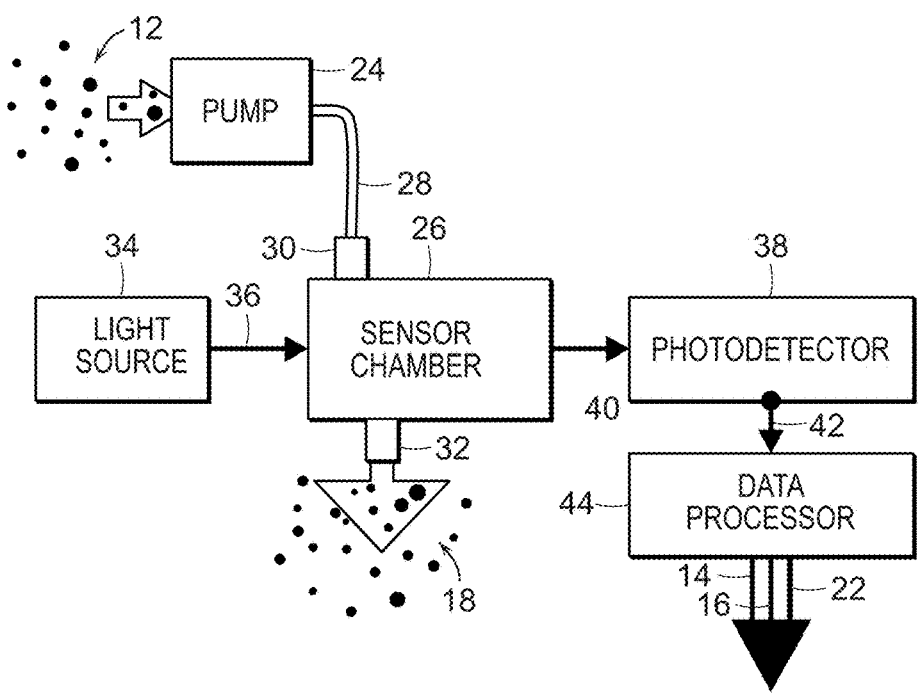
FIG. 2 is a schematic block diagram of the componentry in one aerosol sensor system embodiment, including system inputs and outputs.
Figure 21:
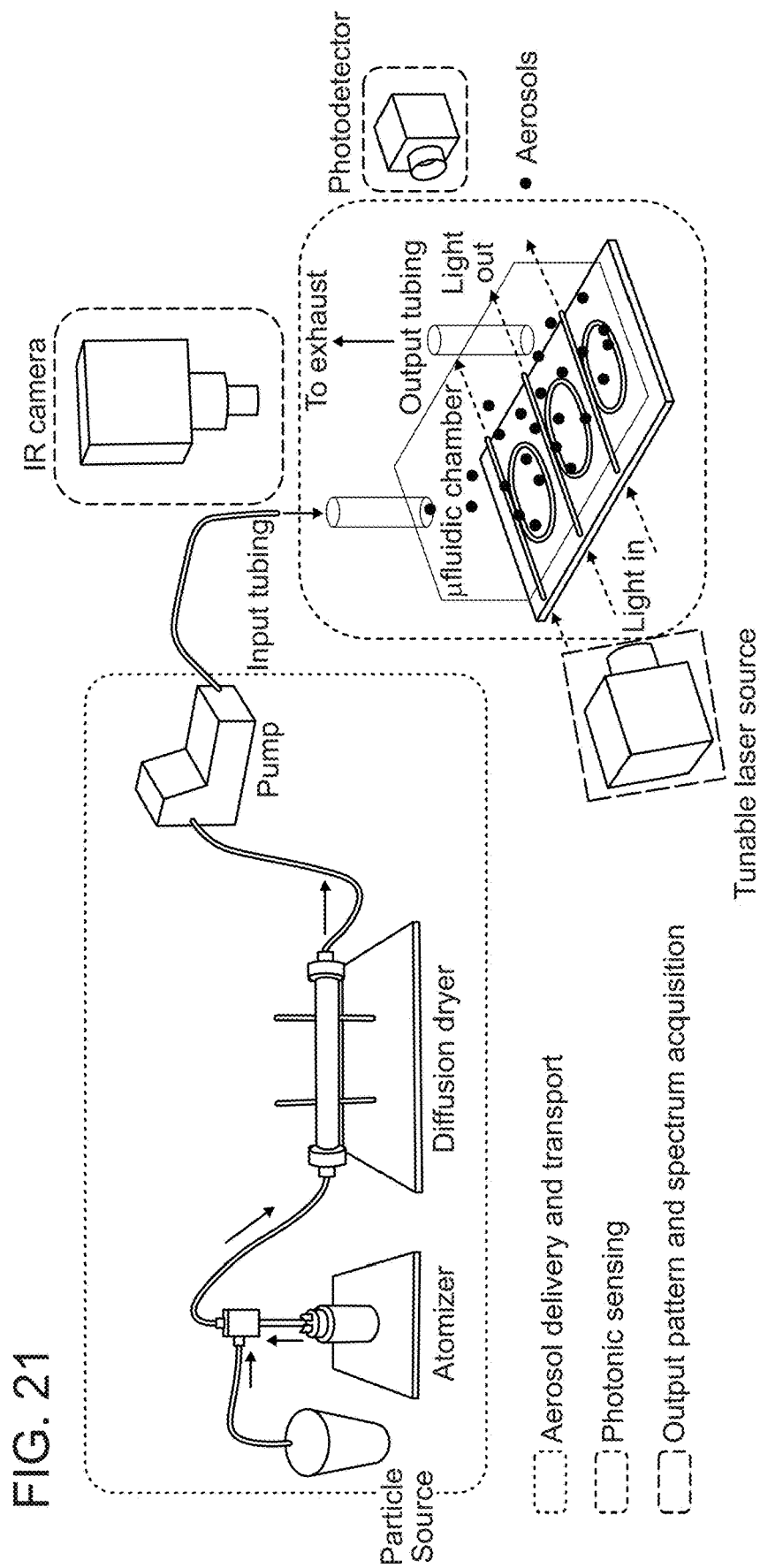

Turning to aerosol sensor system implementation, a microfabricated aerosol sensor including tandem waveguide resonators and other waveguide structures, if desired, is assembled with the other sensor system componentry of FIGS. 1A-1B for calibration and operation. FIG. 21 is a system view of a calibration configuration embodiment for calibrating a set of tandem waveguide resonators prior to operation of the aerosol particle sensor. FIG. 21 is a schematic representation of system componentry shown for clarity as separate macro-scale components. As explained above, it is to be understood that each represented component can be monolithically integrated on a common microfabrication substrate, can be microfabricated on separate substrates that are interconnected, e.g., on a circuit board, or configured separately as-desired; the schematic representation is not meant to require a literal disposition of componentry in the particular arrangement shown.

In a calibration configuration, a microfluidic particle sensing chamber, (µfluidic chamber) is arranged to include a plurality of tandem waveguide resonators, and additional waveguides if desired, to be exposed to a source of known and characterized aerosol particles. The photonic sensing platform provided by the chamber of resonators and waveguides interfaces with an aerosol delivery and transport configuration and photodetection componentry along with image acquisition componentry such as an IR camera, for providing output pattern and spectrum acquisition equipment. A computer or other device can be connected to receive the outputs for implementing the calibration mapping.

To conduct a system calibration, a controlled aerosol is obtained or as shown here, produced, using, e.g., a material for a source of aerosol particle matter. The particle source is atomized and then dried, e.g., with a diffusion dryer, and then pumped, preferably at a constant pressure, and preferably with a regulated flow rate, through input tubing into the microfluidic chamber, with random spatial distribution of the particles around the resonators. A commercial atomizer, e.g., a 3076 atomizer, from TSI, Inc., Auburn, Ill., can be used to aerosolize a liquid, using a compressed air aerosolization technique. Tubing, such as ¼-1 inch outer-diameter tubing, can be employed for the input tubing. Polyurethane hard tubing can be preferred because polyurethane prohibits condensation and sticking of particles on the tubing walls. A commercial dryer, e.g., a 3062 diffusion dryer from TSI, Inc., Auburn, Ill., can be employed. The diffusion dryer can be implemented as, e.g., a cylindrical pipe of about one meter in length. A commercial vacuum pump, such as Kozyvacu TA350, from Kaeser Compressors, Inc., Fredericksburg, Va., can be employed. Suction is only required when the flow rate is not sufficient in the aerosol medium. If an atomizer is employed, suction is not required. A flow rate of about 3 L/min can be preferred, but any suitable flow rate, e.g., between about 0.5 L/min and about 4 L/min, can be employed. The particle input tubing to the sensor chamber is preferably maintained with a constant flow of particles so that there can be assumed a steady state condition for estimating the particle count for the given flow rate.

The microfluidic chamber in which the particle sensing takes place can be implemented, e.g., as an acrylic plastic chamber in which a microfabricated photonic substrate is disposed, and is arranged in a shape and with dimensions that are suitable for a given application. There is no required dimension for the chamber, and individual chamber compartments can be provided as described below; all that is required is that the selected plurality of tandem waveguide resonators be supported within the chamber for interaction with an incoming aerosol sample. The chamber is preferably leak-proof and provides unobstructed exhaust for particles to flow out of the chamber through output tubing.

A tunable laser source or wavelength-multiplexed source as in FIG. 14 is disposed for coupling of laser light into each of the waveguide resonators and other waveguide structures. One or more photodetectors are configured for accepting and detecting light out of each of the ring resonators. Finally, an image acquisition device, such as an IR camera is positioned to image the aerosol within the chamber. The output indications from the photodetector and the camera are sent to suitable computation apparatus for processing and analysis.

The laser can be provided as a commercial laser, e.g., a Luna Technologies, Inc., Coquitlam, BC, Canada, tunable laser for 1500 nm to 1550 nm, or an M Squared Firefly Laser, Glasgow UK, for the MIR spectral range. Edge coupling can be used between the laser and the resonator waveguides with fiber optics, for NIR devices, and free-space coupling can be employed between the laser and the waveguides for MIR devices. A high-aperture focusing lens system can be preferred for free-space coupling. An IR camera can be implemented as, e.g., a Mid-IR $N_2$-cooled indium antimonids such as the IRC806 camera from IRCameras, LLC, Santa Barbara, Calif. All of the laser system, photodetector, and IR camera can be implemented as separate, discrete components, or as monolithically integrated components that are miniaturized and disposed on the platform on which the ring resonators are microfabricated. On-chip laser systems, such as quantum cascade lasers, from BostonElectronics, Brookline, Mass., can be employed.

Figure 22A:
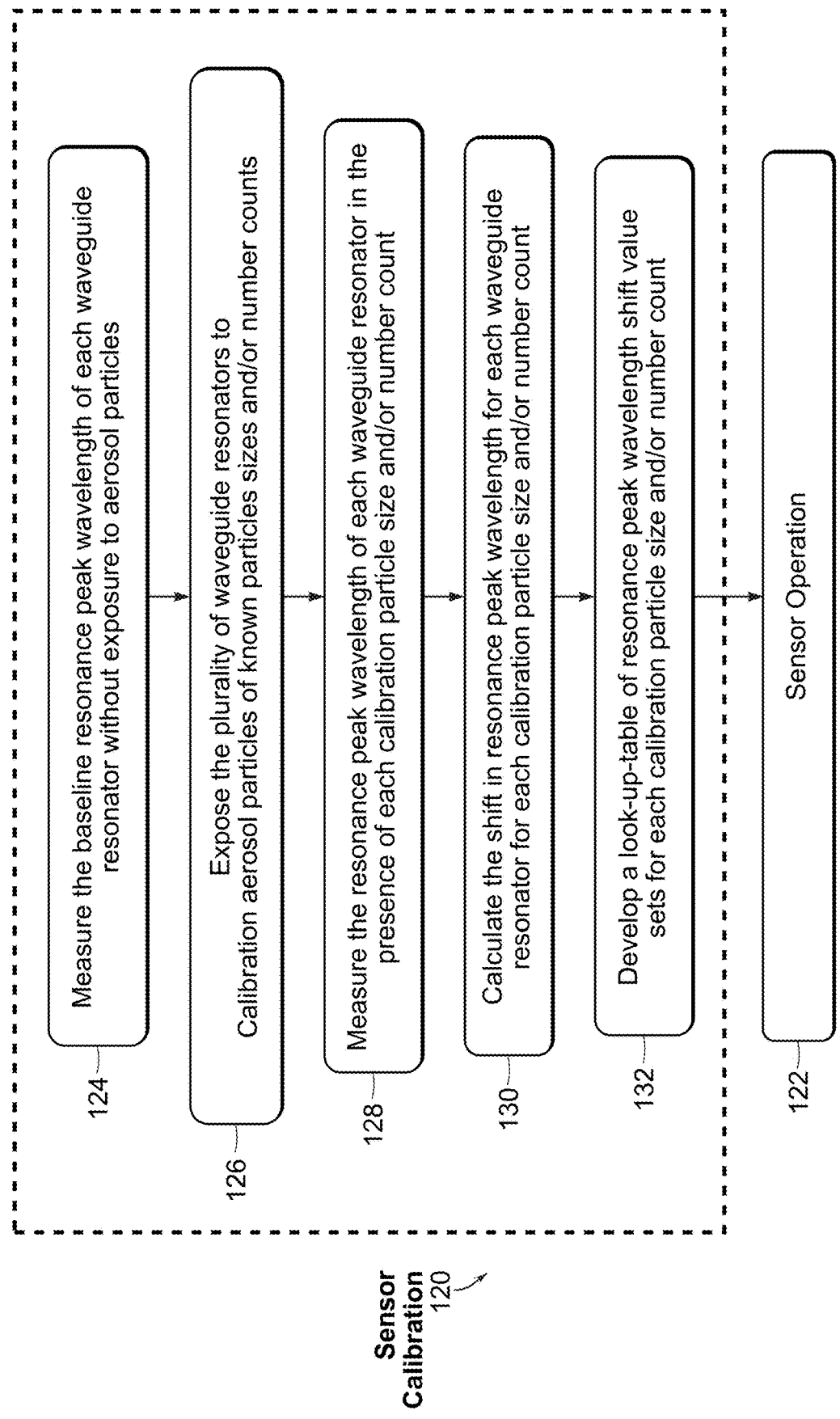
Figure 22B:
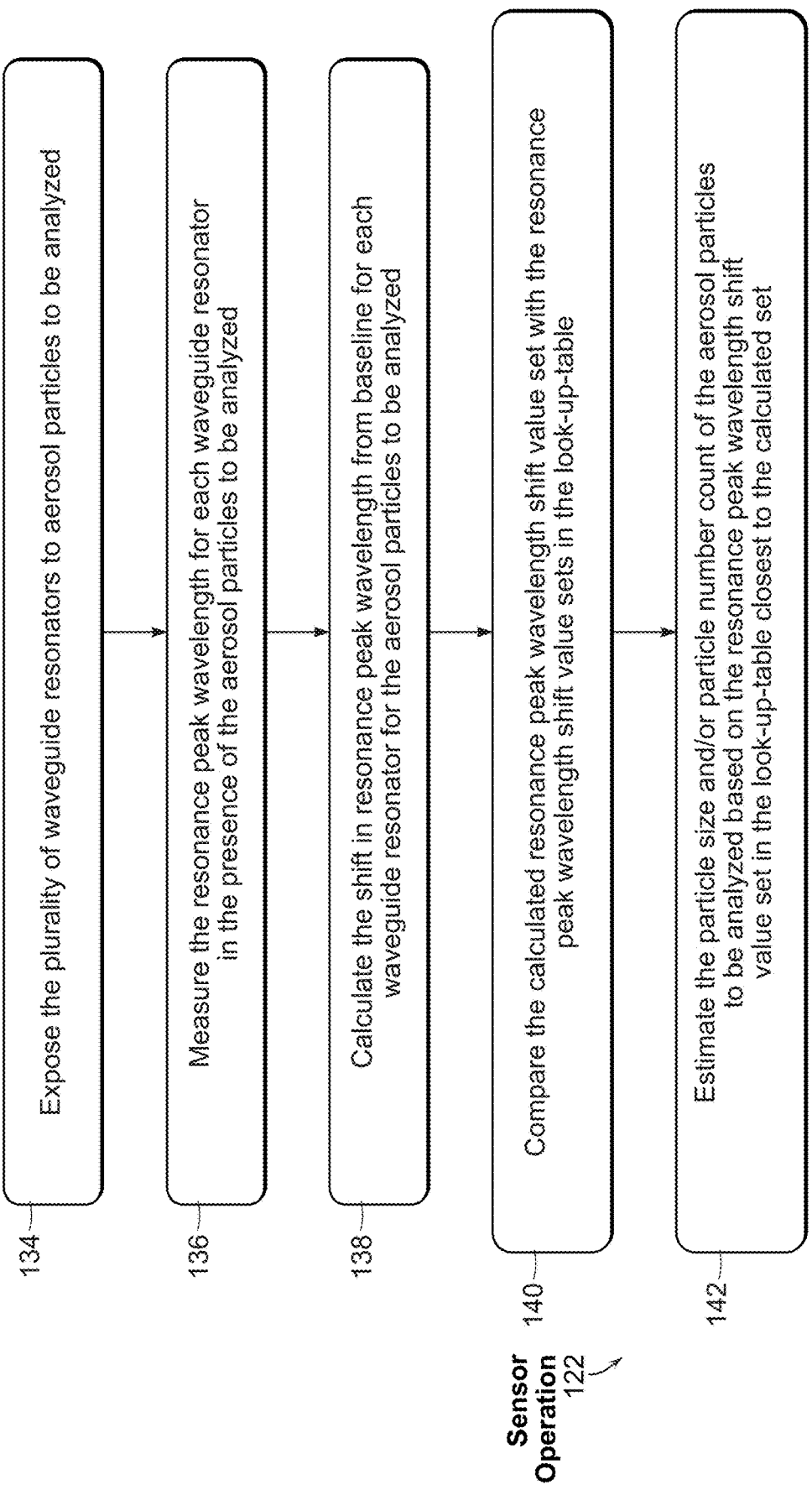

With the aerosol particle sensor calibration system configuration of FIG. 21, then, referring to FIGS. 22A-22B there are conducted the steps for aerosol sensor calibration 120 and for aerosol sensor operation 122, respectively, for determination of physical characteristics of aerosol particles such as aerosol particle size and/or aerosol particle number count. In a calibration process, 120, in a first calibration step 124, the resonance peak wavelength of each waveguide resonator in the plurality of waveguide resonators is measured while light is transmitted through the waveguide resonators, without exposing the waveguide resonators to aerosol particles. A selected gas, and/or air, can be pumped through the chamber during this measurement. This produces a baseline resonance peak wavelength value for each of the waveguide resonators. Once the baseline resonance peak wavelength is measured, then in a next step 126 the plurality of waveguide resonators is exposed to calibration aerosol particles of known size and/or number count, using, e.g., the calibration configuration of FIG. 21. The resonance peak wavelength of each waveguide resonator is measured 128 in the presence of each calibration aerosol particle population, separately for selected aerosol particles sizes and/or aerosol particle number counts. Then there is calculated 130 the shift in resonance peak wavelength between the baseline resonance peak wavelength and the resonance peak wavelength, for each resonator, that was measured in the presence of each population of calibration aerosol particles, for the selected calibration aerosol particle sizes and/or aerosol particle number counts. A look-up-table is then developed 132 with sets of resonance peak wavelength shift values for the plurality of waveguide resonators for each calibration aerosol particle size and/or aerosol particle number count. A mapping like that of FIG. 10 results. With this calibration data, the aerosol sensor system is calibrated and ready for aerosol sensor operation 122.

In operation 122 of the aerosol particle sensor, as shown in FIG. 22B, the plurality of waveguide resonators is exposed 134 to a population of aerosol particles to be analyzed, and the resonant peak wavelength for each waveguide resonator during aerosol exposure is measured 136. Then the shift in resonance peak wavelength between the baseline resonance peak wavelength, measured during calibration, and the resonance peak wavelength that was measured in the presence of the population of aerosol particles to be analyzed, is calculated 138 for each waveguide resonator, producing a set of resonance peak wavelength shift data for the plurality of waveguide resonators. This set of resonance peak wavelength shift data is compared 140 to all of the sets of resonance peak wavelength shift data in the mapping, e.g., a look-up-table, and with the comparison, the aerosol particle size and/or aerosol particle number count for the aerosol particle population to be analysed is estimated 142, based on the resonance peak wavelength shift value set of the look-up-table that is closest to the calculated set. This aerosol sensor operation can then be repeated for a next aerosol particle sample to be analyzed, once the chamber is exhausted, e.g., by pumping air or a selected inert gas through the chamber.

The example methodology shown in FIGS. 22A-22B was directed to particular aerosol particle characteristics, namely, aerosol particle size and/or aerosol particle number count, for clarity in explanation of the methodology. But in further embodiments, as explained above, this methodology can be applied for analyzing a population of aerosol particles for other characteristics, such as aerosol particle shapes, or other aerosol particle characteristics. In general, the methodology is to be applied for analyzing any selected aerosol particle characteristic. No particular aerosol particle characteristic analysis is required.

Figure 23A:
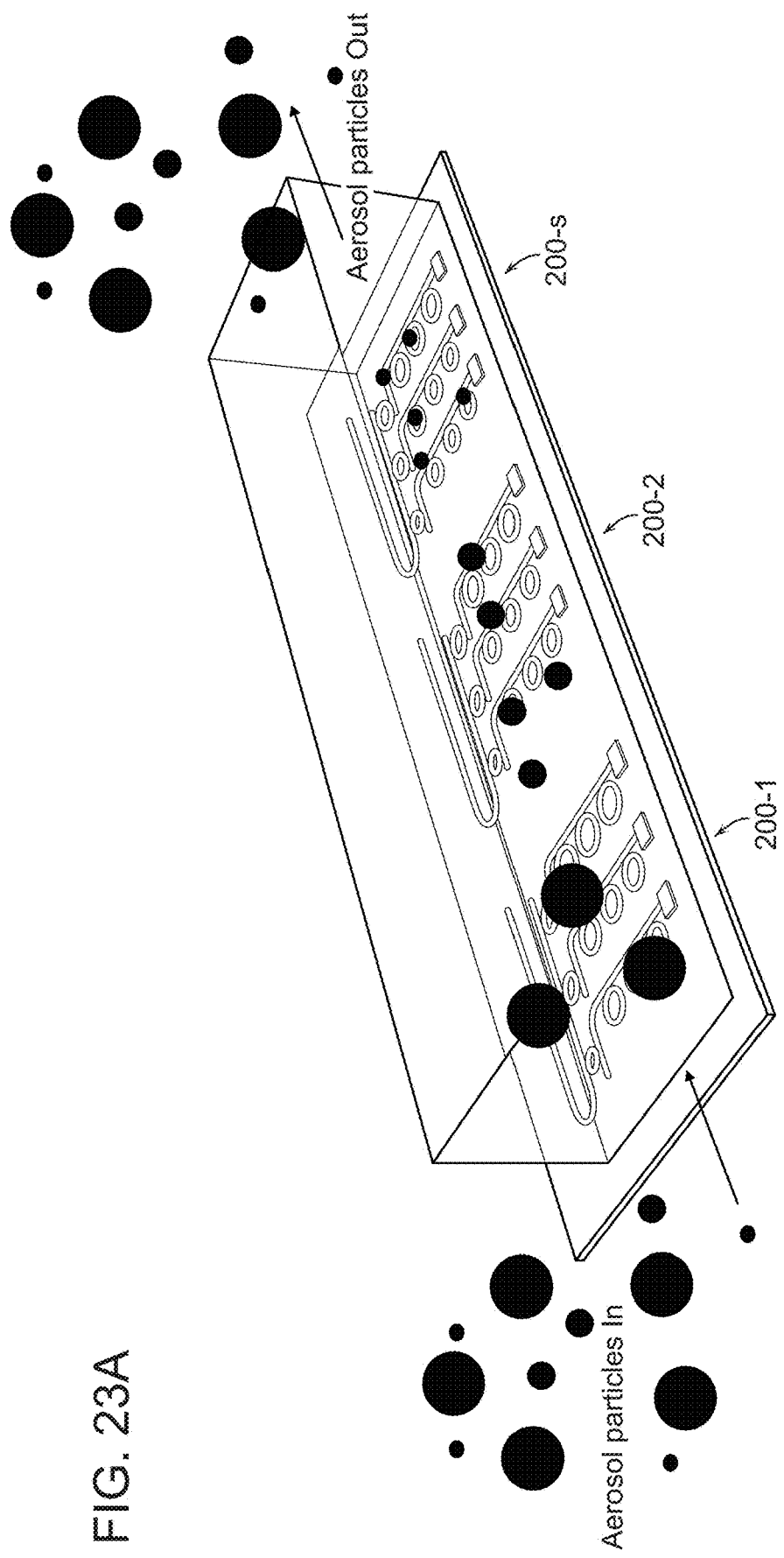

In embodiments provided herein, a set of tandem waveguide resonators can be specifically configured for a selected particle sensing application for conducting the methodology of FIGS. 22A-22B. For example, referring to FIG. 23A, there can be employed a plurality of wavelength resonator arrays 200-1, 200-2, . . . 200-s, up to a number, s, of arrays, each array like the array 47 of FIG. 14. As aerosol particles of different sizes flow into the chamber containing the arrays 200-1, 200-2, . . . 200-s, the particles settle onto the surface of the arrays due to the effect of gravity. Larger, more heavy aerosol particles settle more quickly than smaller, lighter aerosol particles. As a result, the lighter and/or smaller a given aerosol particle, the farther into the chamber the particle travels prior to settling on the surface. This condition is exploited in one embodiment by calibrating a first array 200-1, closest to the aerosol particle input, for relatively larger-sized aerosol particles, a second array 200-2, for relatively smaller-sized aerosol particles, and so on, up to a last array 200-s, farthest from the input, with size calibration for the smallest expected particle. The particles in FIG. 24A are shown grossly out of scale only for clarity in demonstration of this principle. This embodiment enables a natural filtering of aerosol particle sizes to aid in precise analysis of aerosol particles by waveguide resonators that are particularly calibrated for corresponding particle sizes.

Figure 23B:
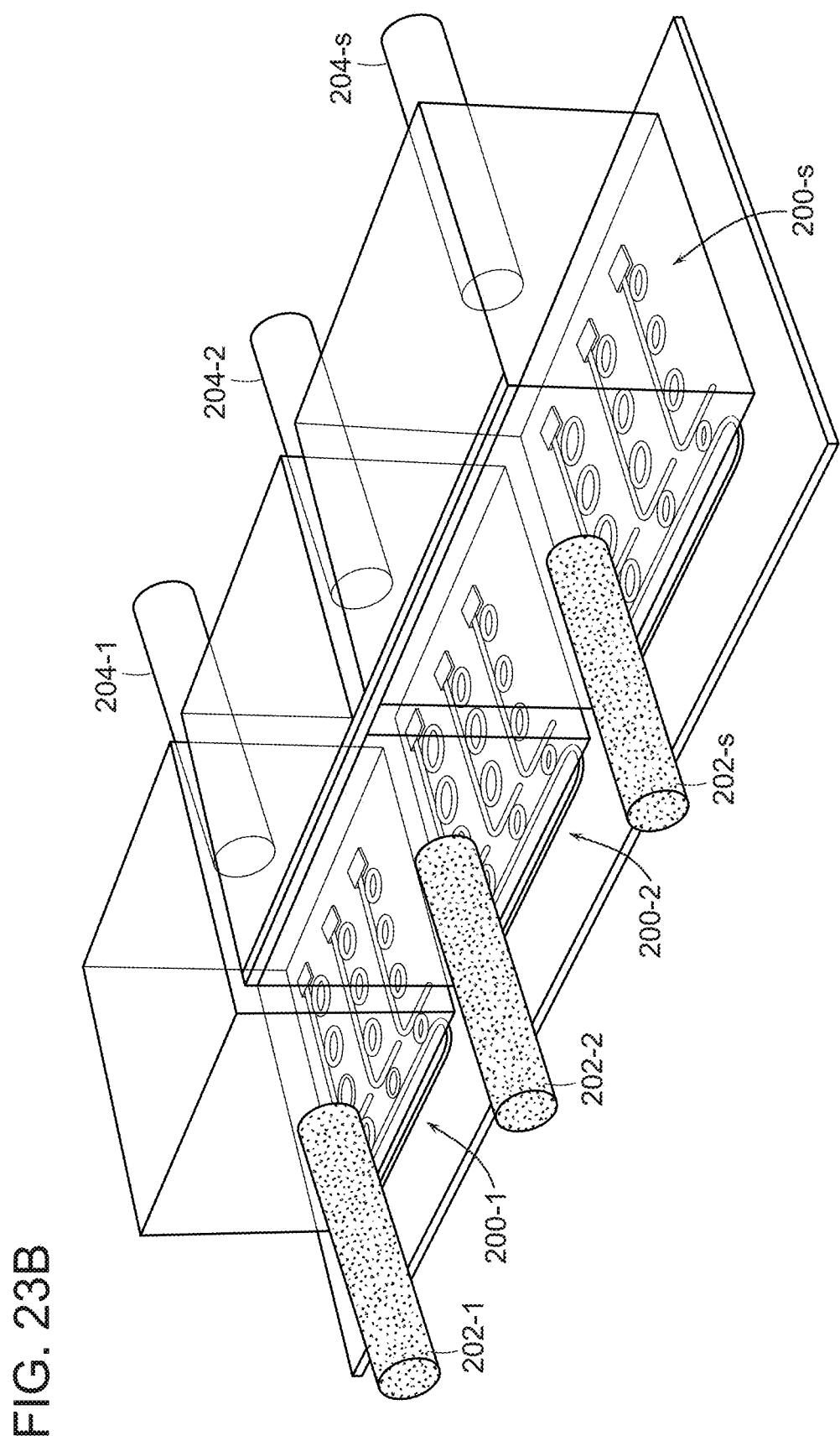

In an alternative embodiment, shown in FIG. 23B, multiple waveguide resonator arrays 200-1, 200-2, . . . , 200-s, up to a number, s, or arrays, are here configured each with a separate corresponding aerosol input 202-1, 202-2, . . . , 202-s, and a separate corresponding aerosol output 204-1, 204-2, . . . 204-s, and if desired, with internal chamber walls to separately isolate each of the waveguide resonator arrays. Each input 202-1, 202-2, . . . , 202-s is configured with a filter that allows a selected aerosol particle size range to enter to the vicinity of a corresponding waveguide resonator array. For example, a first input 202-1 can include a filter to allow aerosol particles only of radii between about 2000 nm and about 5000 nm to be delivered to the first waveguide resonator array 200-1; a second input 202-2 can include a filter to allow aerosol particles only of radii between about 500 nm and about 2000 nm to be delivered to the second waveguide resonator array 200-2; a last input 202-s can include a filter to allow aerosol particles only of radii between about 100 nm and about 500 nm to be delivered to the last waveguide resonator array 200-s. This configuration enables segregation of particles before delivery to the vicinity of waveguide resonators. This paradigm is extended in further embodiments to segregation of incoming aerosol particles by aerosol particle shape, by aerosol particle chemistry, and/or for other aerosol particle characteristics as-desired.

Figure 24B:
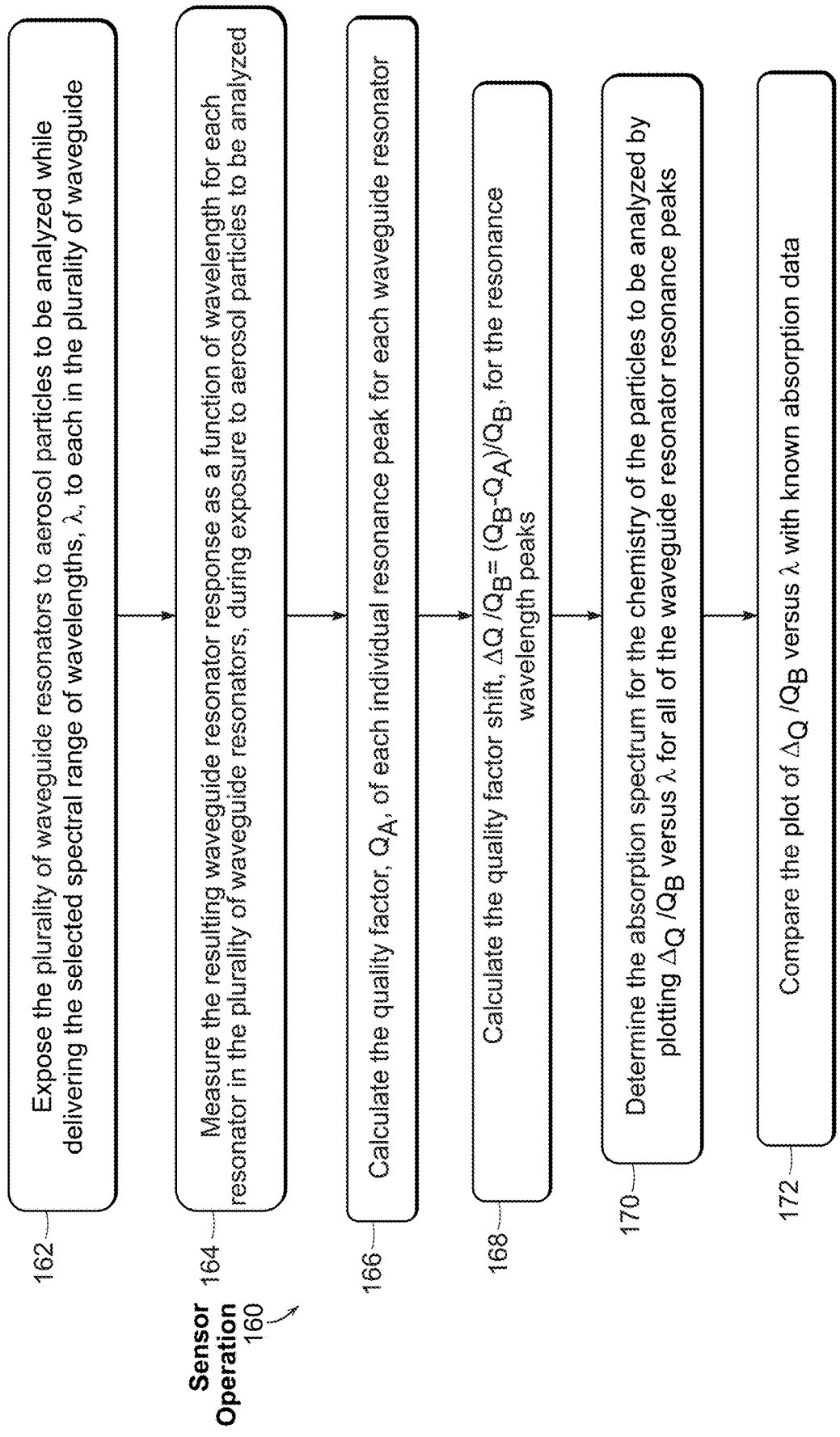

Turning now to FIGS. 24A-24B, there are shown the steps for aerosol sensor calibration 150 and for aerosol sensor operation 160 for determination of chemical characteristics of an aerosol particle population to be analyzed. In a first calibration step 152, a selected spectral wavelength range is delivered to each waveguide resonator in a plurality of waveguide resonators, without exposure of the waveguide resonators to aerosol particles. Then the resulting baseline waveguide resonator response is measured 154 as a function of delivered wavelength for each waveguide resonator in the plurality of waveguide resonators without exposure to aerosol particles. With this measured baseline waveguide resonator response, there is then calculated 156 the baseline quality factor, $Q_B$, of the individual resonance peaks of each waveguide resonator. A reference of the baseline quality factor, $Q_R$, for each resonator waveguide in the plurality of resonator waveguides, can then be produced 158 for use during analysis for aerosol sensor operation 160.

In operation of the aerosol sensor 160 for chemical analysis of aerosol particles, as shown in FIG. 24B, in a first step 162, a plurality of waveguide resonators is exposed aerosol particles to be analyzed while there is delivered a selected spectral wavelength range to each waveguide resonator. Then the resulting waveguide resonator response is measured 164 as a function of wavelength for each waveguide resonator during exposure to aerosol particles to be analyzed. With these measurements, the quality factor, $Q_A$, of each individual resonance peak for each waveguide resonator during aerosol exposure is calculated 166 from the measurements of resonator response in the presence of aerosol particles to be analyzed. Then the quality factor shift, $\phi Q/Q_B = (Q_B - Q_A)/Q_B$ is calculated 168 for each waveguide resonator, and a corresponding absorption spectrum indicative of particle chemistry is determined 170 by plotting $\Delta Q/Q_B$ as a function of wavelength for all waveguide resonator resonance peaks. This plotted spectrum is compared 172 with known absorption spectrum data to identify the chemistry of the aerosol particles to be analyzed.

In the example methodologies of FIGS. 24A-24B for aerosol sensor calibration and operation for chemical characterization of aerosol particles, it is specified to calibrate and expose the plurality of resonator waveguides to a range of spectral wavelengths and to aerosol particles to be analyzed. It is to be understood that in embodiments herein, as few as one waveguide resonator in the plurality can be employed for chemical analysis of aerosol particles; or some subset of the plurality of waveguide resonators can be employed. In other words, not all waveguide resonators in the plurality of resonators need be operated for chemical analysis. In some embodiments, the multiplexing configuration provided for the waveguide resonator array 47 of FIG. 15 can be particularly advantageous, so that different multiples of a wavelength are simultaneously generated and delivered to separate waveguide resonators for simultaneously producing a resonator response across a wavelength spectrum. It can therefore be preferred for many embodiments to employ multiple or all of the waveguide resonators in a plurality of waveguide resonators that are provided for physical characterization of aerosol particles.

Figure 3:
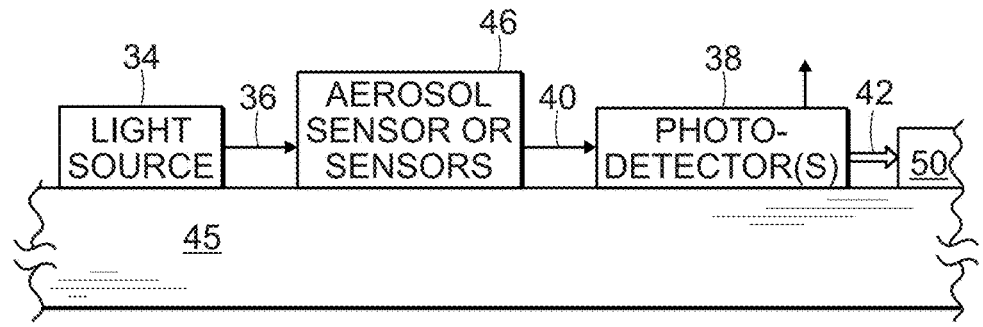
FIG. 3 is a schematic block diagram of aerosol sensor system componentry that is monolithically integrated by microfabrication.
Figure 25:
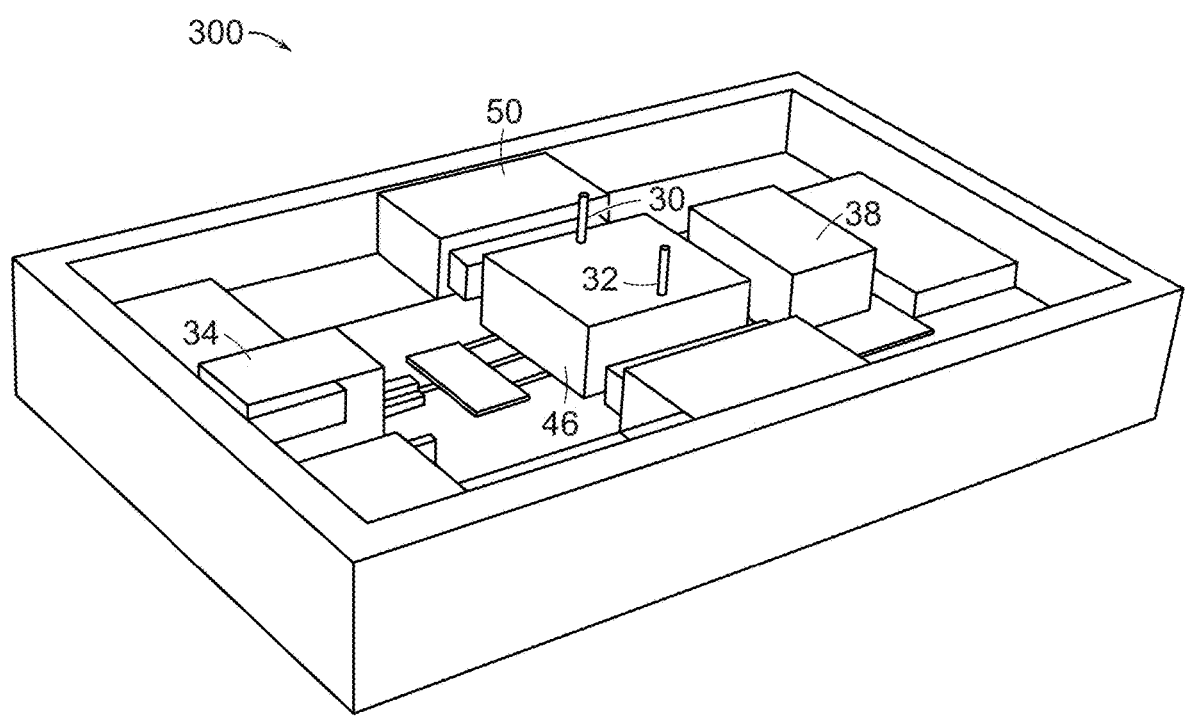

Referring to FIG. 25, there is shown a schematic perspective view of a packaged, portable, compact aerosol sensor system 300 including the microfabricated aerosol sensor componentry shown in FIG. 3. Aerosol particle input 30 and output 32 are provided to a chamber 46 including microfabricated waveguide-based sensors. A microfabricated light source 34 is provided to deliver optical signals to the sensors, and one or more microfabricated photodetectors 38 are provided for detecting output from the sensors, e.g., as taught in US Patent Application Publication No. 2007/0104410, published May 10, 2007, hereby incorporated by reference in its entirety; as taught in US Patent Application Publication No. 2007/0110358, published May 17, 2007, hereby incorporated by reference in its entirety; as taught in "Ge Photodetector monolithically integrated with amorphous Si waveguide on wafer-bonded Ge-on-insulator substrate," Optics Express, Vol. 26, No. 23, 30546, November 2018, hereby incorporated by reference in its entirety; and as taught in "On-chip chalcogenide glass waveguide-integrated mid-infrared PbTe detectors," *Appl. Phys. Letts.*, Vol. 109, 071111, 2016, hereby incorporated by reference in its entirety. Circuitry 50 is provided for processing the signals from the photodetectors.

With the ability to sense all of particle count, particle size, particle chemistry, and other particle characteristics in this compact aerosol sensing system, a wide range of applications are addressed with particularly superior performance. Aerosols that are present in the environment are found to play an important role in climate change. The aerosol sensor provided herein characterizes environmental aerosols with high accuracy and with a compact, portable system that can be employed even at remote locations. For example, aerosol particle populations including carbon-based soot particles, sulfates, nitrates, mineral dust, and other particles can be sensed. Further, the portability and sensitivity of the aerosol sensor enables ease of installation of multiple aerosol sensors to sense and monitor particle emissions at a network of locations, e.g., in different part of a manufacturing operation, at different cites of an industrial or construction location, or other distributed system. There can be accordingly be arranged a sensing network for monitoring over and across a wide site, such as a city and surrounding metropolitan areas for, e.g., pollutants, emissions, chemical or and biological threats, or environmental condition, such as bacteria, fungi, dinoflagellates, sulphur-rich compounds, TNT, and other hazardous aerosol particle materials.

Considering medical applications for the aerosol sensor embodiments provided herein, a range of breath analysis applications are enabled. For example, breath biopsy procedures, in which exhaled breath of a human is analyzed to detect the presence of disease biomarkers, such as lung cancer, is becoming widely employed and can achieve very high accuracy with an embodiment including the aerosol sensor provided herein. Other analyses of breath components can similarly be achieved with the aerosol sensor embodiments provided herein.

The aerosol sensor is also important for drug delivery applications such as pulmonary drug delivery. For example, nebulizers are used to aerosolize drugs for delivery to the inner tract of human lungs. The particle size of an aerosolized drug is crucial in determining the aerosol deposition parameters for drug delivery in the lung. The particle sensor herein enables precise particle characterization to ensure successful nebulizer treatment. In addition, nanoparticles are now employed widely for other drug delivery applications. Nanoparticles are, for many applications, difficult to characterize. The aerosol sensor enables aerosolized nanoparticle size, particle count, and particle chemistry analysis for all such applications. Any nanoparticle population that can be aerosolized in the manner described above can be characterized by the methodology given herein.

It is recognized that those skilled in the art may make various modifications and additions to the embodiments described above without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A photonic aerosol particle sensor comprising:
   a plurality of photonic waveguide resonators, each photonic waveguide resonator comprising a photonic waveguide disposed on an underlying substrate material along a separate waveguide resonator path and having a lateral waveguide width that is different than the lateral waveguide width of other photonic waveguide resonators in the plurality of photonic waveguide resonators, all photonic waveguides in the plurality of photonic waveguide resonators having a common vertical thickness and formed of a common photonic waveguide material having a waveguide material refractive index larger than a substrate material refractive index of the underlying substrate material;
   at least one optical input connection for coupling light into each photonic waveguide in the plurality of photonic waveguide resonators;
   an aerosol particle input for conveying aerosol particles to be analyzed toward the plurality of photonic waveguide resonators;
   an aerosol particle output for conveying aerosol particles away from the plurality of photonic waveguide resonators; and
   at least one optical output connection optically connected to accept light out of the plurality of photonic waveguide resonators to provide a signal indicative of at least one characteristic of the aerosol particles to be analyzed.

2. The photonic aerosol particle sensor of claim 1 wherein the plurality of photonic waveguide resonators comprises a plurality of at least three photonic waveguide resonators.

3. The photonic aerosol particle sensor of claim 1 wherein each photonic waveguide in the plurality of photonic waveguide resonators is disposed along a separate waveguide path selected from ring resonator waveguide path and racetrack resonator waveguide path.

4. The photonic aerosol particle sensor of claim 1 wherein each photonic waveguide in the plurality of photonic waveguide resonators is disposed along a separate ring resonator waveguide path and has a common effective ring resonator waveguide path radius.

5. The photonic aerosol particle sensor of claim 1 wherein each photonic waveguide in the plurality of photonic waveguide resonators has a waveguide cross sectional geometry selected from rectangular, rib, and pedestal.

6. The photonic aerosol particle sensor of claim 1 wherein each photonic waveguide in the plurality of photonic waveguide resonators is formed of a common photonic waveguide material selected from silicon, germanium, silicon carbide, silicon nitride, germanium, and a chalcogenide glass.

7. The photonic aerosol particle sensor of claim 1 wherein each photonic waveguide in the plurality of photonic waveguide resonators is formed of a common photonic waveguide material that supports transmission of light having a wavelength between about 1500 nm and about 1600 nm.

8. The photonic aerosol particle sensor of claim 1 wherein each photonic waveguide in the plurality of photonic waveguide resonators is formed of a common photonic waveguide material that supports transmission of light having a wavelength between about 3.0 microns and about 3.5 microns.

9. The photonic aerosol particle sensor of claim 1 wherein the at least one optical input connection comprises at least one photonic waveguide coupling bus disposed laterally adjacent to and spaced apart from at least one photonic waveguide in the plurality of photonic waveguide resonators for coupling light from a light source to at least one photonic waveguide in the plurality of photonic waveguide resonators.

10. The photonic aerosol particle sensor of claim 9 wherein the at least one photonic waveguide coupling bus comprises a plurality of photonic waveguide coupling buses providing a separate photonic waveguide coupling bus for each photonic waveguide in the plurality of photonic waveguide resonators, each separate waveguide coupling bus disposed laterally adjacent to and spaced apart from a corresponding photonic waveguide in the plurality of photonic waveguide resonators for coupling light from a light source to the corresponding photonic waveguide.

11. The photonic aerosol particle sensor of claim 9 wherein the at least one photonic waveguide coupling bus comprises one photonic waveguide coupling bus disposed laterally adjacent to and spaced apart from all photonic waveguides in the plurality of photonic waveguide resonators for coupling light from a light source to all photonic waveguides in the plurality of photonic waveguide resonators.

12. The photonic aerosol particle sensor of claim 9 wherein the at least one optical input connection further comprises a waveguide input bus having a waveguide coupling region disposed laterally adjacent to and spaced apart from the at least one waveguide coupling bus and having an input connection for providing light from a light source to the at least one waveguide coupling bus.

13. The photonic aerosol particle sensor of claim 1 wherein the at least one optical input connection comprises a plurality of waveguide coupling buses, each waveguide coupling bus disposed lateral adjacent to and spaced apart from at least one photonic waveguide in the plurality of photonic waveguide resonators for coupling light from a light source to each of the at least one photonic waveguides in the plurality of photonic waveguide resonators.

14. The photonic aerosol particle sensor of claim 1 wherein the at least one optical output connection comprises at least one waveguide coupling bus disposed laterally adjacent to and spaced apart from at least one photonic waveguide in the plurality of photonic waveguide resonators for coupling light out of at least one photonic waveguide in the plurality of photonic waveguide resonators.

15. The photonic aerosol particle sensor of claim 1 further comprising:
   a non-resonant photonic waveguide length disposed along a non-resonant waveguide path, the non-resonant photonic waveguide length formed of a photonic waveguide material common with that of the plurality of photonic waveguide resonators and having a vertical thickness common with that of the plurality of photonic waveguide resonators;
   at least one optical input connection for coupling light into the non-resonant photonic waveguide length; and
   at least one optical output connection connected to accept light out of the non-resonant waveguide length to provide a photonic signal indicative of at least one characteristic of the aerosol particles to be analyzed.

16. The photonic aerosol particle sensor of claim 15 wherein the non-resonant photonic waveguide length includes a photonic waveguide path selected from a spiral-shaped path and a paperclip-shaped path.

17. The photonic aerosol particle sensor of claim 1 wherein the at least one optical input connection comprises:
   a plurality of multiplexer photonic waveguide resonators each having a multiplexer photonic waveguide disposed along a separate waveguide path, and each multiplexer photonic waveguide resonator having an effective resonator radius that is different than the effective resonator radius of other multiplexer photonic waveguide resonators; and
   a plurality of waveguide coupling buses, each waveguide coupling bus disposed lateral adjacent to and spaced apart from at least one photonic resonator waveguide in the plurality of photonic waveguide resonators and disposed lateral adjacent to and spaced apart from a corresponding one of the multiplexer photonic waveguide resonators in the plurality of multiplexer photonic waveguide resonators, for coupling light from the corresponding multiplexer photonic waveguide resonator to at least one photonic resonator waveguide.

18. The photonic aerosol particle sensor of claim 1 wherein the at least one optical output connection is connected to accept light out of the plurality of photonic waveguide resonators to provide a photonic signal indicative of an aerosol particle characteristic that includes at least one characteristic selected from aerosol particle size, aerosol particle number count, and aerosol particle chemistry.

19. The photonic aerosol particle sensor of claim 1 wherein the plurality of photonic waveguide resonators is disposed on a microfabrication substrate, and further comprising a laser light source disposed on the microfabrication substrate and optically connected to the at least one optical input connection.

20. The photonic aerosol particle sensor of claim 1 wherein the plurality of photonic waveguide resonators is disposed on a microfabrication substrate, and further comprising at least one photodetector disposed on the microfabrication substrate and optically connected to the at least one optical output connection to provide an electrical signal indicative of at least one aerosol particle characteristic.

21. The photonic aerosol particle sensor of claim 1 further comprising an aerosol sensor chamber in which is disposed the plurality of photonic waveguide resonators, the aerosol particle input being fluidically connected to convey aerosol particles into the aerosol senor chamber and the aerosol particle output being fluidically connected to convey aerosol particles out of the aerosol chamber.

22. The photonic aerosol particle sensor of claim 21 further comprising:
   a laser optically connected to the at least one optical input connection for coupling laser light into each photonic waveguide in the plurality of photonic waveguide resonators; and
   at least one photodetector optically connected to at least one optical output connection connected to accept light out of the plurality of photonic waveguide resonators to provide an electronic signal indicative of at least one characteristic of the aerosol particles to be analyzed.

23. A photonic aerosol particle sensor comprising:
   a plurality of at least three photonic waveguide resonators, each photonic waveguide resonator comprising a photonic waveguide disposed on an underlying substrate material, along a separate waveguide resonator path and having a lateral waveguide width that is different than the lateral waveguide width of other photonic waveguide resonators in the plurality of photonic waveguide resonators, all photonic waveguides in the plurality of photonic waveguide resonators having a common vertical thickness and formed of a common photonic waveguide material having a photonic waveguide refractive index larger than a substrate material refractive index of the underlying substrate material;
   a laser light source;
   at least one photonic waveguide coupling bus optically connected to couple light from the laser light source into each photonic waveguide in the plurality of photonic waveguide resonators and to couple light out of each photonic waveguide in the plurality of photonic waveguide resonators;
   an aerosol particle input for conveying aerosol particles to be analyzed toward the plurality of photonic waveguide resonators;
   an aerosol particle output for conveying aerosol particles away from the plurality of photonic waveguide resonators; and
   at least one photodetector connected to accept light out of the at least one photonic waveguide coupling bus to produce an electronic signal indicative of at least one characteristic of the aerosol particles to be analyzed.

24. A method for sensing aerosol particles comprising:
   conveying aerosol particles to be analyzed toward a plurality of photonic waveguide resonators, each photonic waveguide resonator comprising a photonic waveguide disposed along a separate waveguide resonator path and having a lateral waveguide width that is different than the lateral waveguide width of other photonic waveguide resonators in the plurality of photonic waveguide resonators, all photonic waveguides in the plurality of photonic waveguide resonators having a common vertical thickness and formed of a common photonic waveguide material;
   coupling light into the plurality of photonic waveguide resonators while the aerosol particles are conveyed toward the plurality of photonic waveguide resonators;
   coupling light out of the plurality of photonic waveguide resonators while the aerosol particles are conveyed toward the plurality of photonic waveguide resonators;
   detecting light coupled out of the plurality of photonic waveguide resonators and based on the detected light, determining a resonance peak wavelength of each photonic waveguide resonator in the plurality of photonic waveguide resonators in response to exposure to the aerosol particles;

calculating a difference between a baseline resonance peak wavelength of each photonic waveguide resonator, characteristic of each photonic waveguide resonator absent exposure to the aerosol particles, and the determined resonance peak wavelength of each photonic waveguide resonator in response to exposure to the aerosol particles, to specify a resonance peak wavelength shift value for each photonic waveguide resonator in response to exposure to the aerosol particles;

comparing the specified resonance peak wavelength shift values for the plurality of photonic waveguide resonators with calibration resonance peak wavelength shift values prespecified for the plurality of photonic waveguide resonators for at least one aerosol particle characteristic; and based on the comparison, determining at least one aerosol particle characteristic.

25. The method of claim 24 further comprising a step of determining the baseline resonance peak wavelength of each photonic waveguide resonator, comprising:
coupling light into the plurality of photonic waveguide resonators in the absence of exposure to aerosol particles;
coupling light out of the plurality of photonic waveguide resonators in the absence of exposure to aerosol particles; and
measuring the resonance peak wavelength of each photonic waveguide resonator in the absence of exposure to aerosol particles.

26. The method of claim 24 further comprising a step of producing the calibration resonance peak wavelength shift values, comprising:
coupling light into the plurality of photonic waveguide resonators while calibration aerosol particles having a known characteristic are conveyed toward the plurality of photonic waveguide resonators;
coupling light out of the plurality of photonic waveguide resonators while the calibration aerosol particles are conveyed toward the plurality of photonic waveguide resonators;
detecting light coupled out of the plurality of photonic waveguide resonators and based on the detected light, determining a calibration resonance peak wavelength of each photonic waveguide resonator in the plurality of photonic waveguide resonators in response to exposure to the calibration aerosol particles;
calculating a difference between the baseline resonance peak wavelength of each photonic waveguide resonator and the calibration resonance peak wavelength of each photonic waveguide resonator in response to exposure to the calibration aerosol particles, to specify a calibration resonance peak wavelength shift value for each photonic waveguide resonator in response to exposure to the calibration aerosol particles; and
determining calibration resonance peak wavelength shift values for a plurality of different known aerosol particle characteristics.

27. The method of claim 24 wherein the at least one aerosol particle characteristic for which the calibration resonance peak wavelength shift values are prespecified for the plurality of photonic waveguide resonators includes at least one aerosol particle characteristic selected from particle size, particle number count, and particle chemistry.

28. The method of claim 24 wherein conveying aerosol particles to be analyzed toward a plurality of photonic waveguide resonators comprises conveying aerosolized drug particles toward the plurality of photonic waveguide resonators.

29. The method of claim 24 wherein conveying aerosol particles to be analyzed toward a plurality of photonic waveguide resonators comprises conveying carbon-based aerosol particles toward the plurality of photonic waveguide resonators.

30. The method of claim 24 further comprising:
determining a resonance peak quality factor for each photonic waveguide resonator in the plurality of photonic waveguide resonators in response to exposure to the aerosol particles;
calculating a difference between a baseline resonance peak quality factor of each photonic waveguide resonator, characteristic of each photonic waveguide resonator absent exposure to the aerosol particles, and the determined resonance peak quality factor for each photonic waveguide resonator in response to exposure to the aerosol particles, to specify a quality factor shift value for each photonic waveguide resonator in response to exposure to the aerosol particles;
determining an absorption spectrum corresponding to the quality factor shift value for each photonic waveguide resonator in response to exposure to the aerosol particles while a spectrum of wavelengths is coupled into the plurality of photonic waveguide resonators; and
comparing the determined absorption spectrum with known absorption data to estimate the chemistry of the aerosol particles.

* * * * *